US008961994B2

(12) United States Patent
Ramanathan et al.

(10) Patent No.: US 8,961,994 B2
(45) Date of Patent: Feb. 24, 2015

(54) DNA CONSTRUCTS ELICITING IMMUNE RESPONSE AGAINST FLAVIVIRUS AND EFFECTIVE ADJUVANTS

(75) Inventors: Mathura P. Ramanathan, Ardmore, PA (US); Niranjan Y Sardesai, Blue Bell, PA (US)

(73) Assignee: VGX Pharmaceuticals, LLC, Plymouth Meeting, PA (US)

( * ) Notice: Subject to any disclaimer, the term of this patent is extended or adjusted under 35 U.S.C. 154(b) by 260 days.

(21) Appl. No.: 13/129,599

(22) PCT Filed: Nov. 17, 2009

(86) PCT No.: PCT/US2009/064726

§ 371 (c)(1), (2), (4) Date: Jul. 11, 2011

(87) PCT Pub. No.: WO2010/057159

PCT Pub. Date: May 20, 2010

(65) Prior Publication Data

US 2011/0262394 A1 Oct. 27, 2011

Related U.S. Application Data

(60) Provisional application No. 61/115,535, filed on Nov. 17, 2008.

(51) Int. Cl.

| | |
|---|---|
| ***A61K 39/12*** | (2006.01) |
| ***C12N 15/40*** | (2006.01) |
| ***C12N 15/62*** | (2006.01) |
| *A61K 39/00* | (2006.01) |

(52) U.S. Cl.

CPC ............. *A61K 39/12* (2013.01); *A61K 2039/53* (2013.01); *A61K 2039/55527* (2013.01); *C12N 2770/24134* (2013.01)

USPC ................... 424/218.1; 514/44 R; 536/23.72; 536/23.4; 435/461

(58) Field of Classification Search

None

See application file for complete search history.

(56) References Cited

U.S. PATENT DOCUMENTS

| | | | | |
|---|---|---|---|---|
| 2004/0254365 | A1* | 12/2004 | Lee | 536/23.72 |
| 2007/0087354 | A1 | 4/2007 | Charneau | |
| 2008/0044808 | A1 | 2/2008 | Song | |
| 2008/0091135 | A1 | 4/2008 | Draghia-Akli et al. | |
| 2009/0074781 | A1 | 3/2009 | Chen | |
| 2009/0156787 | A1* | 6/2009 | Draghia-Akli et al. | 530/387.1 |

OTHER PUBLICATIONS

Alka et al (Medical Microbiology and Immunology 196:227-231, 2007).*
Alka et al (Med Microbiol Immuno 196:227-231, 207).*
Martina et al (Vaccine 26:153-157, 2008, available online Nov. 20, 2007).*
Chu et al (Journal of Immunology 178:2699-2705, 2007).*
Mota et al (Vaccine 23:3469-3476, 2005).*
Garmory et al (Genetic Vaccines and Therapy 2003, 1:2, pp. 1-5).*
Svanholm et al (Journal of Immunological Methods 28:121-130, 1999).*
Yan et al (Vaccine 27:431-440, 2009, available online Nov. 18, 2008).*
Kim et al (Gene Therapy 10:1266-1273, 2003).*
Genbank AF196835, Dec. 7, 2000.*
Genbank AAF20092, Dec. 7, 2000.*
Haas et al (Current Biology 6: 315-324, 1996).*
Kutzler Michele A et al: "Coimmunization with an optimized IL-15 plasmid results in enhanced function and longevity of CD8 T cells that are partially independent of CD4 T cell help.", Journal of Immunology vol. 175, No. 1, Jul. 1, 2005 pp. 112-123.
EMBL accession #U44971. (Aug. 3, 1996) [Retrieved from the Internet Apr. 28, 2010:<http://srs.ebi.ac.uklsrsbinicgi-biniwgetz?-e+[EMBL:U44971]+-newld].
EMBL accession #DQ646699. (Dec. 25, 2006) [Retrieved from the Internet Apr. 28, 2010: <http://srs.ebi.ac.uklsrsbin/cgi-binlwgetz?-e+[EMBL:DQ646699]+-newld].

* cited by examiner

*Primary Examiner* — Mary E Mosher
(74) *Attorney, Agent, or Firm* — Thomas Kim

(57) ABSTRACT

Aspects of the present invention relate to isolated nucleic acids that encode a consensus DIII domain of protein E and vaccines made using same, and also methods for using the aforementioned to generate in a host an immune response against multiple serotypes of flavivirus, particularly West Nile virus and Japanese encephalitis virus.

17 Claims, 7 Drawing Sheets

Figure 1A

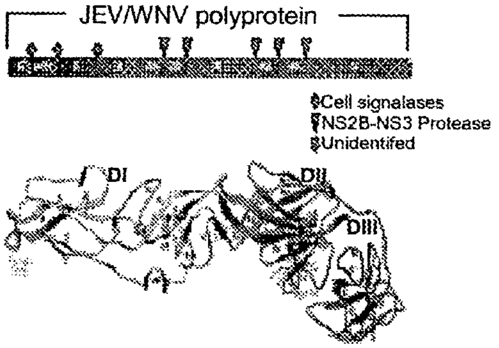

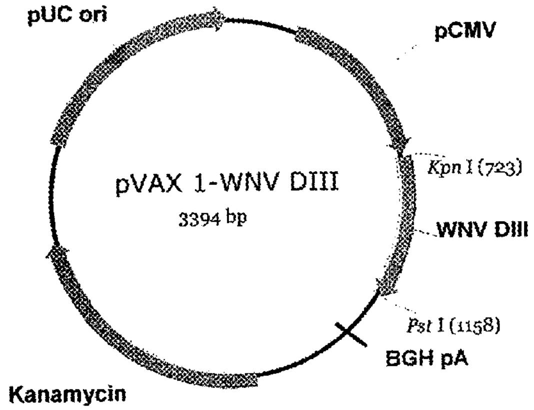

Figure 1B

JEV DIII Consensus Sequence:
MDWTWILFLVAAATRVHSALKGTTYGMCTEKFSFAKNPADTGHGTVV
IELSYSGSDGPCKIPIVSVASLNDMTPVGRLVTVNPFVATSSANSKV
LVEMEPPFGDSYIVVGRGDKQINHHWHKAGSTLGKAFSTTLKGAQ*

WNV DIII Consensus Sequence:
MDWTWILFLVAAATRVHSQLKGTTYGVCSKAFKFLGTPADTGHGTVV
LELQYTGTDGPCKVPISSVASLNDLTPVGRLVTVNPFVSVATANAKV
LIELEPPFGDSYIVVGRGEQQINHHWHKSGSSIGKAFTTTLKGAQ*

WN/JEV DIII Consensus Sequence:
MDWTWILFLVAAATRVHSALKGTTYGMCTSKFSKAKNPPDTGHGTVV
IELSYSTSTGPCKIPIVSVASLNDMTPVGRLVTVNPFVATSSANSKV
LVEMEPPFGDSYIVVGRGDKQINHHWHKAGSTLGKAFSTTLKGAQ*

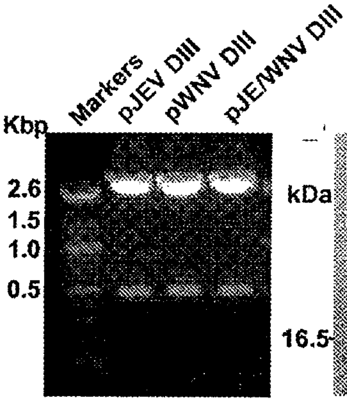

Figure 1C

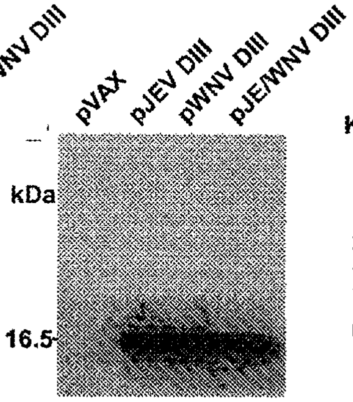

Figure 1D

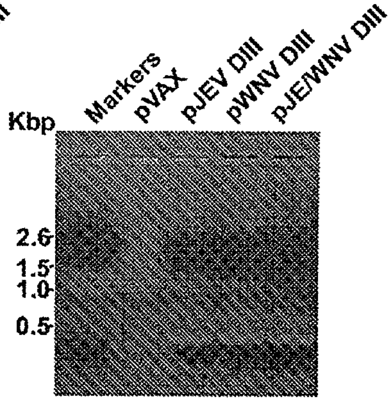

Figure 1E

Electroporation (Via Cellectra™) of Balb/C mice
4 mice/group (20ug DNA/mouse)

Day 0    Day 14    Day 28    Day 35
                              Sacrifice
                              ELISpot
                              ELISA Animal Groups:
1. JEV DIII              6. JEV DIII + pVAX1-IL15
2. WNV DIII              7. WNV DIII + pVAX1-IL15
3. JE/WNV DIII           8. JE/WNV DIII + pVAX1-IL15
4. JEV + WNV DIII        9. JEV + WNV DIII + pVAX1-IL15
5. pVAX                  10. pVAX + pVAX1-IL15

SEQUENCE LISTING

<160> NUMBER OF SEQ ID NOS: 15

<210> SEQ ID NO 1
<211> LENGTH: 139
<212> TYPE: PRT
<213> ORGANISM: Artificial Sequence
<220> FEATURE:
<223> OTHER INFORMATION: JEV DIII consensus sequence

<400> SEQUENCE: 1

```
Met Asp Trp Thr Trp Ile Leu Phe Leu Val Ala Ala Ala Thr Arg Val
1               5                   10                  15

His Ser Ala Leu Lys Gly Thr Thr Tyr Gly Met Cys Thr Glu Lys Phe
            20                  25                  30

Ser Phe Ala Lys Asn Pro Ala Asp Thr Gly His Gly Thr Val Val Ile
        35                  40                  45

Glu Leu Ser Tyr Ser Gly Ser Asp Gly Pro Cys Lys Ile Pro Ile Val
    50                  55                  60

Ser Val Ala Ser Leu Asn Asp Met Thr Pro Val Gly Arg Leu Val Thr
65                  70                  75                  80

Val Asn Pro Phe Val Ala Thr Ser Ser Ala Asn Ser Lys Val Leu Val
                85                  90                  95

Glu Met Glu Pro Pro Phe Gly Asp Ser Tyr Ile Val Val Gly Arg Gly
            100                 105                 110

Asp Lys Gln Ile Asn His His Trp His Lys Ala Gly Ser Thr Leu Gly
        115                 120                 125

Lys Ala Phe Ser Thr Thr Leu Lys Gly Ala Gln
    130                 135
```

<210> SEQ ID NO 2
<211> LENGTH: 139
<212> TYPE: PRT
<213> ORGANISM: Artificial Sequence
<220> FEATURE:
<223> OTHER INFORMATION: WNV DIII Consensus Sequence

<400> SEQUENCE: 2

```
Met Asp Trp Thr Trp Ile Leu Phe Leu Val Ala Ala Ala Thr Arg Val
1               5                   10                  15

His Ser Gln Leu Lys Gly Thr Thr Tyr Gly Val Cys Ser Lys Ala Phe
            20                  25                  30

Lys Phe Leu Gly Thr Pro Ala Asp Thr Gly His Gly Thr Val Val Leu
        35                  40                  45

Glu Leu Gln Tyr Thr Gly Thr Asp Gly Pro Cys Lys Val Pro Ile Ser
    50                  55                  60

Ser Val Ala Ser Leu Asn Asp Leu Thr Pro Val Gly Arg Leu Val Thr
65                  70                  75                  80

Val Asn Pro Phe Val Ser Val Ala Thr Ala Asn Ala Lys Val Leu Ile
                85                  90                  95

Glu Leu Glu Pro Pro Phe Gly Asp Ser Tyr Ile Val Val Gly Arg Gly
            100                 105                 110

Glu Gln Gln Ile Asn His His Trp His Lys Ser Gly Ser Ser Ile Gly
        115                 120                 125

Lys Ala Phe Thr Thr Thr Leu Lys Gly Ala Gln
    130                 135
```

<210> SEQ ID NO 3
<211> LENGTH: 139

-continued

<212> TYPE: PRT
<213> ORGANISM: Artificial Sequence
<220> FEATURE:
<223> OTHER INFORMATION: JW DIII Consensus Sequence

<400> SEQUENCE: 3

```
Met Asp Trp Thr Trp Ile Leu Phe Leu Val Ala Ala Ala Thr Arg Val
1               5                   10                  15

His Ser Ala Leu Lys Gly Thr Thr Tyr Gly Met Cys Thr Ser Lys Phe
            20                  25                  30

Ser Lys Ala Lys Asn Pro Pro Asp Thr Gly His Gly Thr Val Val Ile
        35                  40                  45

Glu Leu Ser Tyr Ser Thr Ser Thr Gly Pro Cys Lys Ile Pro Ile Val
    50                  55                  60

Ser Val Ala Ser Leu Asn Asp Met Thr Pro Val Gly Arg Leu Val Thr
65                  70                  75                  80

Val Asn Pro Phe Val Ala Thr Ser Ser Ala Asn Ser Lys Val Leu Val
                85                  90                  95

Glu Met Glu Pro Pro Phe Gly Asp Ser Tyr Ile Val Val Gly Arg Gly
            100                 105                 110

Asp Lys Gln Ile Asn His His Trp His Lys Ala Gly Ser Thr Leu Gly
        115                 120                 125

Lys Ala Phe Ser Thr Thr Leu Lys Gly Ala Gln
    130                 135
```

<210> SEQ ID NO 4
<211> LENGTH: 423
<212> TYPE: DNA
<213> ORGANISM: Artificial Sequence
<220> FEATURE:
<223> OTHER INFORMATION: JEV DIII

<400> SEQUENCE: 4

```
atggactgga cctggatcct gttcctggtg gctgctgcca ctagagtgca cagcgccctg     60

aagggcacca cctacggcat gtgcaccgag aagttcagct tcgccaagaa ccccgccgac    120

accggccacg gcaccgtggt gatcgagctg tcctacagcg gcagcgacgg cccctgcaag    180

atccccatcg tgagcgtggc cagcctgaac gacatgaccc ccgtgggccg gctggtgacc    240

gtgaacccct tcgtggccac ctccagcgcc aacagcaagg tgctggtcga gatggaaccc    300

cccttcggcg acagctacat cgtggtgggc aggggcgaca agcagatcaa ccaccactgg    360

cacaaggccg gcagcaccct gggcaaggcc ttcagcacca cactgaaggg cgcccagtga    420

tga                                                                  423
```

<210> SEQ ID NO 5
<211> LENGTH: 423
<212> TYPE: DNA
<213> ORGANISM: Artificial Sequence
<220> FEATURE:
<223> OTHER INFORMATION: WNV DIII

<400> SEQUENCE: 5

```
atggactgga cctggatcct gttcctggtg gctgctgcca ctagggtgca cagcctccag     60

ctgaagggca ccacctacgg cgtgtgcagc aaggccttca agttcctggg cacccctgcc    120

gataccggcc acggcaccgt ggtgctggaa ctccagtaca ccggcaccga cggcccctgc    180

aaggtgccca tcagcagcgt ggccagcctg aacgacctga cccccgtggg ccggctggtg    240

accgtgaacc ccttcgtgag cgtggccacc gccaacgcca aggtgctgat cgagctggaa    300
```

```
ccccccttcg gcgacagcta catcgtggtg ggcaggggcg agcagcagat caaccaccac    360

tggcacaaga gcggcagcag catcggcaag gcctttacca ccaccctgaa gggcgcctga    420

tga                                                                  423


<210> SEQ ID NO 6
<211> LENGTH: 423
<212> TYPE: DNA
<213> ORGANISM: Artificial Sequence
<220> FEATURE:
<223> OTHER INFORMATION: JW DIII

<400> SEQUENCE: 6

atggactgga cctggatcct gttcctggtg gctgctgcca ctagagtgca cagcgccctg     60

aagggcacca cctacggcat gtgcaccagc aagttcagca aggccaagaa cccccccgac    120

accggccacg gcaccgtggt gatcgagctg tcctacagca ccagcaccgg cccctgcaag    180

atccccatcg tgagcgtggc cagcctgaac gacatgaccc ccgtgggccg gctggtgacc    240

gtgaacccct tcgtggccac ctccagcgcc aacagcaagg tgctggtcga gatggaaccc    300

cccttcggcg acagctacat cgtggtgggc aggggcgaca agcagatcaa ccaccactgg    360

cacaaggccg gcagcaccct gggcaaggcc ttcagcacca cactgaaggg cgcccagtga    420

tga                                                                  423


<210> SEQ ID NO 7
<211> LENGTH: 18
<212> TYPE: PRT
<213> ORGANISM: Artificial Sequence
<220> FEATURE:
<223> OTHER INFORMATION: IgE leader

<400> SEQUENCE: 7

Met Asp Trp Thr Trp Ile Leu Phe Leu Val Ala Ala Ala Thr Arg Val
1               5                   10                  15

His Ser


<210> SEQ ID NO 8
<211> LENGTH: 72
<212> TYPE: DNA
<213> ORGANISM: Artificial Sequence
<220> FEATURE:
<223> OTHER INFORMATION: IgE Leader

<400> SEQUENCE: 8

ggtaccggat ccgccaccat ggactggacc tggattctgt tcctcgtggc tgctgctaca     60

agagtgcaca gc                                                         72


<210> SEQ ID NO 9
<211> LENGTH: 122
<212> TYPE: PRT
<213> ORGANISM: Artificial Sequence
<220> FEATURE:
<223> OTHER INFORMATION: JEV DIII consensus sequence

<400> SEQUENCE: 9

Met Ala Leu Lys Gly Thr Thr Tyr Gly Met Cys Thr Glu Lys Phe Ser
1               5                   10                  15

Phe Ala Lys Asn Pro Ala Asp Thr Gly His Gly Thr Val Val Ile Glu
            20                  25                  30

Leu Ser Tyr Ser Gly Ser Asp Gly Pro Cys Lys Ile Pro Ile Val Ser
```

-continued 35 40 45

Val Ala Ser Leu Asn Asp Met Thr Pro Val Gly Arg Leu Val Thr Val
50 55 60

Asn Pro Phe Val Ala Thr Ser Ser Ala Asn Ser Lys Val Leu Val Glu
65 70 75 80

Met Glu Pro Pro Phe Gly Asp Ser Tyr Ile Val Val Gly Arg Gly Asp
85 90 95

Lys Gln Ile Asn His His Trp His Lys Ala Gly Ser Thr Leu Gly Lys
100 105 110

Ala Phe Ser Thr Thr Leu Lys Gly Ala Gln
115 120

<210> SEQ ID NO 10
<211> LENGTH: 122
<212> TYPE: PRT
<213> ORGANISM: Artificial Sequence
<220> FEATURE:
<223> OTHER INFORMATION: WNV DIII consensus sequence

<400> SEQUENCE: 10

Met Gln Leu Lys Gly Thr Thr Tyr Gly Val Cys Ser Lys Ala Phe Lys
1 5 10 15

Phe Leu Gly Thr Pro Ala Asp Thr Gly His Gly Thr Val Val Leu Glu
20 25 30

Leu Gln Tyr Thr Gly Thr Asp Gly Pro Cys Lys Val Pro Ile Ser Ser
35 40 45

Val Ala Ser Leu Asn Asp Leu Thr Pro Val Gly Arg Leu Val Thr Val
50 55 60

Asn Pro Phe Val Ser Val Ala Thr Ala Asn Ala Lys Val Leu Ile Glu
65 70 75 80

Leu Glu Pro Pro Phe Gly Asp Ser Tyr Ile Val Val Gly Arg Gly Glu
85 90 95

Gln Gln Ile Asn His His Trp His Lys Ser Gly Ser Ser Ile Gly Lys
100 105 110

Ala Phe Thr Thr Thr Leu Lys Gly Ala Gln
115 120

<210> SEQ ID NO 11
<211> LENGTH: 122
<212> TYPE: PRT
<213> ORGANISM: Artificial Sequence
<220> FEATURE:
<223> OTHER INFORMATION: JW DIII consensus sequence

<400> SEQUENCE: 11

Met Ala Leu Lys Gly Thr Thr Tyr Gly Met Cys Thr Ser Lys Phe Ser
1 5 10 15

Lys Ala Lys Asn Pro Pro Asp Thr Gly His Gly Thr Val Val Ile Glu
20 25 30

Leu Ser Tyr Ser Thr Ser Thr Gly Pro Cys Lys Ile Pro Ile Val Ser
35 40 45

Val Ala Ser Leu Asn Asp Met Thr Pro Val Gly Arg Leu Val Thr Val
50 55 60

Asn Pro Phe Val Ala Thr Ser Ser Ala Asn Ser Lys Val Leu Val Glu
65 70 75 80

Met Glu Pro Pro Phe Gly Asp Ser Tyr Ile Val Val Gly Arg Gly Asp
85 90 95

-continued

```
Lys Gln Ile Asn His His Trp His Lys Ala Gly Ser Thr Leu Gly Lys
            100                 105                 110

Ala Phe Ser Thr Thr Leu Lys Gly Ala Gln
        115                 120


<210> SEQ ID NO 12
<211> LENGTH: 372
<212> TYPE: DNA
<213> ORGANISM: Artificial Sequence
<220> FEATURE:
<223> OTHER INFORMATION: JEV DIII DNA

<400> SEQUENCE: 12

atggccctga agggcaccac ctacggcatg tgcaccgaga agttcagctt cgccaagaac     60

cccgccgaca ccggccacgg caccgtggtg atcgagctgt cctacagcgg cagcgacggc    120

ccctgcaaga tccccatcgt gagcgtggcc agcctgaacg acatgacccc cgtgggccgg    180

ctggtgaccg tgaacccctt cgtggccacc tccagcgcca acagcaaggt gctggtcgag    240

atggaacccc ccttcggcga cagctacatc gtggtgggca ggggcgacaa gcagatcaac    300

caccactggc acaaggccgg cagcaccctg ggcaaggcct tcagcaccac actgaagggc    360

gcccagtgat ga                                                        372


<210> SEQ ID NO 13
<211> LENGTH: 372
<212> TYPE: DNA
<213> ORGANISM: Artificial Sequence
<220> FEATURE:
<223> OTHER INFORMATION: WNV DIII DNA

<400> SEQUENCE: 13

atgctccagc tgaagggcac cacctacggc gtgtgcagca aggccttcaa gttcctgggc     60

acccctgccg ataccggcca cggcaccgtg gtgctggaac tccagtacac cggcaccgac    120

ggcccctgca aggtgcccat cagcagcgtg gccagcctga acgacctgac ccccgtgggc    180

cggctggtga ccgtgaaccc cttcgtgagc gtggccaccg ccaacgccaa ggtgctgatc    240

gagctggaac ccccccttcgg cgacagctac atcgtggtgg gcaggggcga gcagcagatc    300

aaccaccact ggcacaagag cggcagcagc atcggcaagg cctttaccac caccctgaag    360

ggcgcctgat ga                                                        372


<210> SEQ ID NO 14
<211> LENGTH: 372
<212> TYPE: DNA
<213> ORGANISM: Artificial Sequence
<220> FEATURE:
<223> OTHER INFORMATION: JW DIII DNA

<400> SEQUENCE: 14

atggccctga agggcaccac ctacggcatg tgcaccagca agttcagcaa ggccaagaac     60

ccccccgaca ccggccacgg caccgtggtg atcgagctgt cctacagcac cagcaccggc    120

ccctgcaaga tccccatcgt gagcgtggcc agcctgaacg acatgacccc cgtgggccgg    180

ctggtgaccg tgaacccctt cgtggccacc tccagcgcca acagcaaggt gctggtcgag    240

atggaacccc ccttcggcga cagctacatc gtggtgggca ggggcgacaa gcagatcaac    300

caccactggc acaaggccgg cagcaccctg ggcaaggcct tcagcaccac actgaagggc    360

gcccagtgat ga                                                        372
```

-continued

```
<210> SEQ ID NO 15
<211> LENGTH: 12
<212> TYPE: DNA
<213> ORGANISM: Artificial Sequence
<220> FEATURE:
<223> OTHER INFORMATION: Kozak sequence

<400> SEQUENCE: 15

ggtaccgcca cc                                                          12
```

DNA CONSTRUCTS ELICITING IMMUNE RESPONSE AGAINST FLAVIVIRUS AND EFFECTIVE ADJUVANTS

BACKGROUND

The Japanese encephalitis virus (JEV) serocomplex-group consists of mosquito-borne flaviviruses, which include West Nile virus (WNV) and JEV, and both may cause severe encephalitis in humans. WNV has spread rapidly across the United States since its introduction in 1999 and its geographical distribution within the western hemisphere is expected to further expand, whereas, JEV is the most common cause of viral encephalitis in Southeast Asia, China and India. Currently, there is no FDA approved specific treatment for both, though there are attempts to develop vaccines against both viruses.

The flaviviruses West Nile virus (WNV) and Japanese encephalitis virus (JEV) are responsible for a large proportion of viral encephalitis in humans. WNV infects a wide range of avian and mammalian species including humans. WNV has also been shown to be transmitted through blood transfusion, organ transplantation, and breast-feeding. The West Nile encephalitis (WNV) virus covers a large geographical area that includes the south of Europe, Africa, central Asia, and more recently North America. The virus often produces symptoms of meningoencephalitis in Israel, Egypt, India and Pakistan. In Egypt, it is responsible for 3% of all meningitis and aseptic encephalitis. JEV is the single-most important cause of viral encephalitis in Asia, with case fatality rates averaging 30%. JEV is a major problem in South-East Asia, India, and China, where the virus is endemic. In recent years, JEV has spread to other geographic areas such as Australia, and Pakistan, and has thus become an important emerging virus infection in these areas.

Japanese encephalitis (JE) is an inflammatory disease in the central nervous system including the cerebrum, the cerebellum, and the spinal cord. Vaccination against JEV using a mouse brain-derived, inactivated vaccine has been shown to be very effective and has led to a decreased disease burden. However, there are concerns about the immunogenicity and the safety of this vaccine. A live-attenuated and a cell culture-based JEV vaccine that are produced on primary hamster kidney (PHK) cells have been licensed for us in China and have been shown to be safe and effective. However, since PHK is not an approved cell line for production of human vaccine, many countries will not use this JEV vaccine.

JEV infections are regarded as one of the most serious viral causes of encephalitis, with a mortality of up to 30-50% and high percentage of neurological sequelae in survivors[8]. Thus, mass immunization programs against Japanese encephalitis are generally recommended for populations residing in the endemic areas by regional and internal public-health authorities, including WHO. In developed, non-endemic countries, JE is regarded as a rare and exotic disease. But in recent decades, cases reports of infections in tourists and other travelers from non-endemic regions have been reported almost every year. However, vaccine coverage in the population of international travelers at risk is very low, which is not only due to a lack of awareness of the disease on the part of travelers and their travel health advisers, but also because of fear of the potential adverse reactions associated with the currently licensed mouse-brain-derived JEV vaccine JE-VAXR[33].

JE-VAXR is a formalin-inactivated vaccine that is produced form mouse brain and licensed for use in children in Japan and for travelers and military personnel in the United States and some European countries. Requirement for multiple-dose regimen and problems with reactogenicity have complicated its use. An affordable vaccine that elicits durable immunity without the need for frequent boosters is needed for control of JE in developing countries. Mouse-brain derived JEV vaccines have been widely used in various countries in Asia and in some developed countries for decades. In adults immunized in Australia, Europe and North America, serious adverse reactions have been reported, consisting of urticaria or angiooedema and, in some cases, dyspnoea. The occurrence of these adverse reactions various and ranges from less than 1 to 104 per 10000 injections, with anaphylaxis as one of the major causes for concern.

The E protein of flaviviruses is the most immunogenic and suitable for the purpose of vaccine development. The protein E consists of three structural domains (DI, DII and DIII), of which DIII contains predominantly sub-complex, and type-specific epitopes. Several vaccines based on DIII have been shown to be immunogenic and effective under certain conditions.

DIII proteins are highly conserved between several WNV and JEV strains. Approximately WNV DIII shares overall amino acid identity and similarity values with JEV DIII of 81 and 94%, respectively. DIII functions as a receptor binding domain, forming a continuous polypeptide segment that can fold independently. Certainly mutations within DIII have shown to affect virulence and tropism of flaviviruses. rDIII is quite a stable protein and hence can become an attractive antigen. The lack of glycosylation of the protein during bacterial expression in prokaryotic cells most likely would not affect its antigenicity since native DIII is not glycosylated as well. Recombinant DIII of JEV and dengue virus has been shown to be immunogenic and protective in mice challenged with the respective virulent viruses, underlining the suitability of DIII base vaccine formulations against flaviviruses. However, in earlier attempts, it was clear that a relatively high concentration of rDIII was needed for induction of neutralizing antibody responses, indicating that rDIII is poorly immunogenic.

A recent molecular analysis of strain of JEV from Asia classified the strain into four distinct genotypic groups[37]. Because the JEV vaccines that are currently available are only based on one strain of JE, this high level of sequence diversity has led to questions and concern about the cross-protective effect of JEV vaccines against circulating strain JEV[12, 13].

DNA vaccines have several advantages over traditional vaccines such as live attenuated virus and recombinant protein-based vaccines in the context of immune therapy[24-26]. DNA vaccines appear to be very well tolerated in humans. Preclinical safety studies indicate that there was little evidence of plasmid integration and DNA vaccines can also be used for repeat administration as the efficacy of plasmid vectors are not influenced by pre-existing neutralizing antibodies. Furthermore, DNA vaccines appear to be very stable and simple to produce. However, initial studies reported that DNA vaccines exhibited low potency in large animals and humans.

Complicating matters for vaccine development, the RNA genome of flaviviruses have high rates of mutation and therefore the JEV circulating in human populations in Asia and Australia are genetically diverse[35,36], although it is generally conceded that all strains in circulation belong to a single serotype defined by neutralization[37].

There still remains a need for a safe and effective JEV vaccine to protect mammals against multiple JEV and WNV serotypes. There also remains a need for an effective adjuvant that can effectively enhance the immune response of a DNA vaccine.

SUMMARY OF THE INVENTION

An aspect of the present invention includes isolated nucleic acids that encode consensus DIII domain of protein E. These nucleic acids can include the nucleotide sequences: (a) SEQ ID NOS: 12, 13, or 14; (b) a nucleotide sequence that encodes an amino acid sequence of SEQ ID NOS: 9, 10, or 11; or (c) a complement of (a) or (b). In another aspect of the present invention, there are genetic constructs that comprise the isolated nucleic acids provided herein. In some embodiments, the genetic construct can include a Kozak sequence GGT ACC GCC ACC (SEQ ID NO.15) and/or a leader sequence that is selected from a portion of IgG or IgE.

In still another aspect of the present invention, there are polypeptides comprising an amino acid sequence comprising: (a) SEQ ID NOS: 9, 10 or 11; or (b) a fragment of (a).

There are aspects of the invention that are DNA vaccines capable of generating in a host an immune response against a plurality of WNV and JEV serotypes, the vaccine comprising: (a) a genetic construct comprising a promoter operably linked to a coding sequence comprising the isolated nucleic acids provided herein; and (b) a pharmaceutically acceptable excipient; wherein, the genetic construct is capable of expressing the consensus DIII domain of protein E antigen in a cell of the host in a quantity effective to elicit an immune response.

In an aspect of the invention, there are methods of eliciting an immune response against a plurality of flavivirus virus serotypes in a host, comprising: (a) delivering the vaccines provided herein to the tissue of the host; and (b) electroporating cells of the tissue using an electroporation device that delivers a pulse of energy effective to permit entry of the genetic construct of the vaccine into the cells.

BRIEF DESCRIPTION OF THE DRAWINGS

The numerous objects and advantages of the present invention may be better understood by those skilled in the art by reference to the accompanying figures, in which:

FIGS. 1A-E: FIG. 1A, organization of flaviviral polyprotein with cleavage sites catalyzed by viral and host cell proteases. A three dimensional conformation of flaviviral E is shown to have three distinct domains, I, II and III. On the right side, plasmid map reveals various elements of vaccine constructs used in this study. FIG. 1B, the consensus amino-acid sequence of DV-U is given. JEV DIII consensus sequence SEQ ID NO:1 is shown. WNV DIII consensus sequence SEQ ID NO:2 is shown. WN/JEV DIII consensus sequence SEQ ID NO:3 is shown. IgE-leader sequence for maximizing the secretion process is underlined. FIG. 1C, restriction digestion of JEV DIII, chimeric JE/WNV DIII and WNV DIII JE/WNV DIII fragments indicates the length of DIII coding region (435 bp). On the left end of the lanes, the DNA ladders are shown. FIG. 1D, in vitro expression of DNA vaccine constructs. 35S-labeled gene products generated from DNA vaccine constructs were resolved in a SDS gel, as described in Materials and Methods. The protein products corresponded to the mobility of approximately 16.5 kDa in mass. Lack of corresponding protein product from pVAX empty vector indicates specificity of this reaction. FIG. 1E, expression analysis DIII-vaccine constructs in RD cells. Cells were transfected with vaccine constructs and two days post transfection, they were analyzed for the presence of DIII-specific mRNA transcripts by RT-PCR. Mock-transfected cells failed to indicate appropriate amplified product. Using appropriate primers, about 435-bp products were observed from DIII-construct transfected cells confirming the presence of corresponding DIII-encoding transcripts.

FIG. 2A. Localization of three different IL15 isoforms. HeLa cells were transfected with plasmids expressing SSP or LSP or OPT IL15 isoforms and were analyzed by immunofluorescence assay after 36 hours of transfection. The cells were fixed, incubated with monoclonal anti-IL15 antibody, followed by incubation with anti-mouse FITC-conjugated secondary antibody. DAPI was used to counter stain the nuclear contents of the cells. Empty vector was used as negative control and the mock-transfected cells did not yield any specific staining (a-c). The IL15-SSP isoform is not secreted, but rather stored intracellularly appearing in nuclear components (d-f), whereas the IL15-LSP isoform (g-i) and human codon optimized IL15 (j-l) are associated with secreted IL15 as clearly revealed in the cytoplasmic regions. FIG. 2B, secretion level of IL15 isoforms. RD cells were transfected with IL15 expression constructs (1 ug/well) and after two days, the supernatants were analyzed for the presence of secreted IL15 protein by ELISA. IL15 ECRO expression construct yielded highest level of IL15 secretion. FIG. 2C, in order to compare the level of secretion, the amount of secreted from IL15 LSP and OPT constructs were shown as fold increase over the SSP form.

FIG. 1A. The schematic plan for vaccination and immunization is indicated. BALB/c mice were immunized two weeks apart with 20×g vaccine constructs or pVAX empty vector via CELLECTRA® electroporator (Inovio Pharmaceuticals, Blue Bell Pa.) and sacrificed one week later. FIG. 1B, anti-DIII serum specifically reacts with purified DIII fragments. Serum from DIII DNA-vaccinated mice was incubated for one hour at 37° C. on 96-well Ni-chelated plates with 1 ug/well of purified DIII protein samples. The production of appropriate antibodies was detected using anti-mouse IgG HRP with routine color development procedures. The plates were read at 450 nm. Values represent the mean (±}S.D) of triplicate wells.

DETAILED DESCRIPTION OF PREFERRED EMBODIMENTS

Figure 2A:
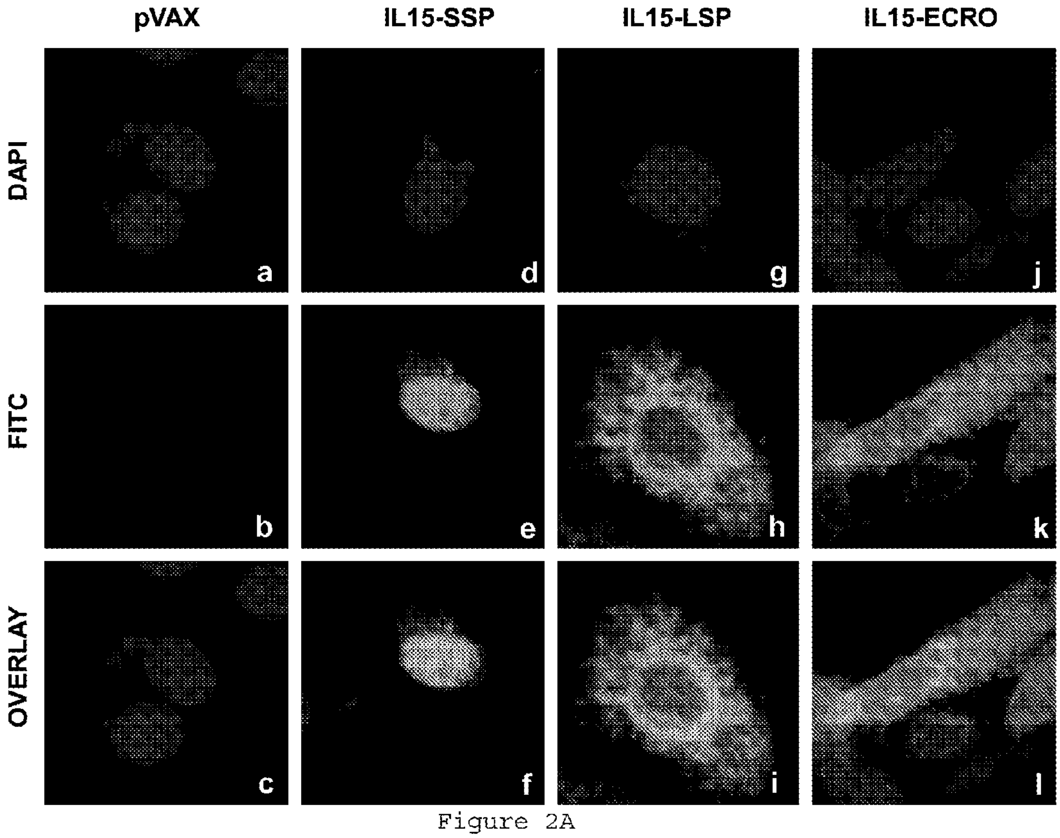
FIGS. 2A-C.

The following abbreviated, or shortened, definitions are given to help the understanding of the preferred embodiments of the present invention. The abbreviated definitions given here are by no means exhaustive nor are they contradictory to the definitions as understood in the field or dictionary meaning. The abbreviated definitions are given here to supplement or more clearly define the definitions known in the art.

DEFINITIONS

Sequence homology for nucleotides and amino acids as used herein may be determined using FASTA, BLAST and Gapped BLAST (Altschul et al., *Nuc. Acids Res.,* 1997, 25, 3389, which is incorporated herein by reference in its entirety) and PAUP* 4.0b10 software (D. L. Swofford, Sinauer Associates, Massachusetts). Briefly, the BLAST algorithm, which stands for Basic Local Alignment Search Tool is suitable for determining sequence similarity (Altschul et al., J. Mol. Biol., 1990, 215, 403-410, which is incorporated herein by reference in its entirety). Software for performing BLAST analyses is publicly available through the National Center for Biotechnology Information. One measure of similarity provided by the BLAST algorithm is the smallest sum probability (P(N)), which provides an indication of the probability by which a match between two nucleotide sequences would occur by chance. For example, a nucleic acid is considered similar to another if the smallest sum probability in comparison of the test nucleic acid to the other nucleic acid is less than about 1, preferably less than about 0.1, more preferably less than about 0.01, and most preferably less than about 0.001. "Percentage of similarity" can be calculated using PAUP* 4.0b10 software (D. L. Swofford, Sinauer Associates, Massachusetts). The average similarity of the consensus sequence is calculated compared to all sequences in the phylogenic tree.

"Complement" or "complementary" as used herein means a nucleic acid can mean Watson-Crick (e.g., A-T/U and C-G) or Hoogsteen base pairing between nucleotides or nucleotide analogs of nucleic acid molecules.

As used herein, the term "expressible form" refers to nucleic acid constructs that contain the necessary regulatory elements operable linked to a coding sequence that encodes a protein such that when present in the cell of the individual, the coding sequence will be expressed.

The term "constant current" is used herein to define a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

The term "feedback" or "current feedback" is used interchangeably and means the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. Preferably, the feedback is accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. In some embodiments, the feedback loop is instantaneous as it is an analog closed-loop feedback.

The terms "electroporation," "electro-permeabilization," or "electro-kinetic enhancement" ("EP") as used interchangeably herein refer to the use of a transmembrane electric field pulse to induce microscopic pathways (pores) in a biomembrane; their presence allows biomolecules such as plasmids, oligonucleotides, siRNA, drugs, ions, and water to pass from one side of the cellular membrane to the other.

The term "decentralized current" is used herein to define the pattern of electrical currents delivered from the various needle electrode arrays of the electroporation devices described herein, wherein the patterns minimize, or preferably eliminate, the occurrence of electroporation related heat stress on any area of tissue being electroporated.

The term "feedback mechanism" as used herein refers to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. The term "impedance" is used herein when discussing the feedback mechanism and can be converted to a current value according to Ohm's law, thus enabling comparisons with the preset current. In a preferred embodiment, the "feedback mechanism" is performed by an analog closed loop circuit.

The term "immune response" is used herein to mean the activation of a host's immune system, e.g., that of a mammal, in response to the introduction of a flavivirus consensus antigen via the provided DNA plasmid vaccines. The immune response can be in the form of a cellular or humoral response, or both.

The term "consensus" or "consensus sequence" is used herein to mean a synthetic nucleic acid sequence, or corresponding polypeptide sequence, constructed based on analysis of an alignment of multiple subtypes of a flavivirus antigen. Consensus flavivirus antigens include DIII domains of E protein of west nile virus (WNV) and Japanese encephalitis virus (JEV) or chimeric sequences combining elements of both sequences.

The term "fragment" as used herein means a nucleic acid, or a portion thereof, that encodes a polypeptide capable of eliciting an immune response in a mammal substantially similar to that of the non-fragment for at least one of the consensus DIII antigens. The fragments can be DNA fragments selected from at least one of the various encoding nucleotide sequences of the present invention, including SEQ ID NOS: 12, 13, and 14. The DNA fragments can be 30 or more nucleotides in length, 45 or more, 60 or more, 75 or more, 90 or more, 120 or more, 150 or more, 180 or more, 210 or more, 240 or more, 270 or more, 300 or more, 360 or more, or 400 or more in length. DNA fragments can comprise coding sequences for the immunoglobulin leader such as IgE or IgG sequences.

DNA fragments can be fewer than 10 nucleotides, fewer than 20, fewer than 30, fewer than 40, fewer than 50, fewer than 60, fewer than 75, fewer than 90, fewer than 120, fewer than 150, fewer than 180, fewer than 210, fewer than 240, fewer than 270, fewer than 300, fewer than 360, or fewer than 400.

“Fragment” can also mean a polypeptide fragments capable of eliciting an immune response in a mammal substantially similar to that of the non-fragment for at least one DIII protein (or antigen). The fragment can be polypeptide fragment selected from at least one of the various encoding polypeptide sequences of the present invention, including SEQ ID NOS: 9, 10, and 11. Polypeptide fragment can be analyzed to contact at least one antigenic epitope as provided by a publicly available database. Polypeptides DIII fragments can further comprise amino acid sequences for the immunoglobulin leader such as IgE or IgG. The polypeptide fragments can be 30 or more amino acids in length, 45 or more, 60 or more, 75 or more, 90 or more, 120 or more, or 130 amino acids or more in length.

Polypeptide fragments can be fewer than 10 amino acids, fewer than 20, fewer than 30, fewer than 40, fewer than 50, fewer than 60, fewer than 75, fewer than 90, fewer than 120, or fewer than 130 amino acids in length.

The term “adjuvant” is used herein to mean any molecule added to the DNA plasmid vaccines described herein to enhance antigenicity of the desired antigen, preferably a consensus antigen, encoded by the DNA plasmids and encoding nucleic acid sequences described hereinafter.

The term “subtype” or “serotype” is used herein interchangeably and means genetic variants of a virus, or an epitope therein, such that one subtype is recognized by an immune system apart from a different subtype, or in other words, one subtype has different immunogenic characteristics than another subtype.

Three types of DIII sequences: consensus JEV DIII, consensus WNV DIII and. chimeric sequence JEV sequence in which WNV DIII residues (denoted as JW DIII or JEV/WN DIII or WN/JEV DIII) [16, 17] that have been shown to be determinants in the induction of neutralizing antibody against WNV were incorporated at corresponding positions. All these sequences are consensus across twenty strains individually. Use of consensus sequences for DNA vaccine development is one of the latest cutting edge technologies in the fight against infectious diseases[22, 23]. Based on the consensus sequence, synthetic human codon optimized sequences were generated for immunization in this study.

Encoding Nucleotides

An aspect of the present invention includes isolated nucleic acids that encode consensus DIII domain of protein E. These nucleic acids can include the nucleotide sequences: (a) SEQ ID NOS: 12, 13, or 14; (b) a nucleotide sequence that encodes an amino acid sequence of SEQ ID NOS: 9, 10, or 11; or (c) a complement of (a) or (b). In another aspect of the present invention, there are genetic constructs that comprise the isolated nucleic acids provided herein. In some embodiments, the genetic construct can include a Kozak sequence GGT ACC GCC ACC (SEQ ID NO.15) and/or a leader sequence that is selected from a portion of IgG or IgE, preferably IgE, and more preferably IgE having the sequence of SEQ ID NO: 8.

The consensus DIII protein can be encoded by a consensus DIII nucleic acid, a variant thereof or a fragment thereof. The consensus DIII nucleic acid can be codon optimized and/or RNA optimized. The consensus DIII nucleic acid sequence can comprise a leader sequence. The leader sequence can be 5' of the DIII coding sequence. The consensus DIII protein encoded by this sequence can comprise an N-terminal leader followed by a consensus DIII protein. The N-terminal leader can be IgE or IgG.

Polypeptide/Antigens

Provided herein are antigens capable of eliciting an immune response in a mammal against one or more flavivirus serotypes, particularly various serotypes of West Nile virus and Japanese encephalitis virus. The antigen can be capable of eliciting an immune response in a mammal against one or more flavivirus serotypes, including against one or more pandemic strains. The antigen can comprise epitopes that make them particularly effective as immunogens against which anti-flavivirus immune responses can be induced.

In one aspect of the present invention, there are polypeptides comprising the amino acid sequence that is a consensus DIII protein. The DIII protein can comprise: (a) SEQ ID NOS: 9, 10 or 11; or (b) a fragment of (a). The consensus DIII protein can further comprise on its N-terminal an IgE or IgG leader amino acid sequence. The IgE leader amino acid sequence can be that set forth in SEQ ID NO: 7. The consensus DIII protein with an IgE leader sequence can have the amino acid sequence of SEQ ID NO: 1, 2, or 3, which also includes JEV DIII, WNV DIII, or JW DIII, respectively.

Vaccines

There are aspects of the invention that are DNA vaccines capable of generating in a host an immune response against a plurality of WNV and JEV serotypes, the vaccine comprising: (a) a genetic construct comprising a promoter operably linked to a coding sequence comprising the isolated nucleic acids provided herein; and (b) a pharmaceutically acceptable excipient; wherein, the genetic construct is capable of expressing the consensus DIII domain of protein E antigen in a cell of the host in a quantity effective to elicit an immune response.

In some embodiments, the DNA vaccines of the present invention include genetic constructs that have regulatory elements necessary for gene expression of a nucleic acid molecule.

In some embodiments of the present invention, the DNA vaccines can further include an adjuvant. The adjuvants can be selected from: α-interferon, γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE, IL-12, IL-15, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, IL-28, MCP-1, MIP-1a, MIP-1p, IL-8, RANTES, L-selectin, P-selectin, E-selectin, CD34, GlyCAM-1, MadCAM-1, LFA-1, VLA-1, Mac-1, pl50.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof or combinations thereof. The vaccine may also be administered in combination with CTACK protein, TECK protein, MEC protein or functional fragments thereof.

In some preferred embodiments, the adjuvant is IL-15 along with one or more additional adjuvants.

Genetic Constructs

Provided herein is a genetic construct that can comprise the nucleic acid encoding the DIII antigen. The genetic construct can be present in the cell as a functioning extrachromosomal molecule comprising the nucleic acid encoding the DIII antigen, preferably a DNA plasmid. The genetic construct comprising the nucleic acid encoding the DIII antigen can be linear minichrosome including centromere, telomers. The genetic construct can also be part of a genome of a recombinant viral vector, including recombinant adenovirus, recombinant adenovirus associated virus and recombinant vaccinia. The genetic construct can be part of the genetic material in attenuated live microorganisms or recombinant microbial vectors which live in cells. The genetic constructs can comprise regulatory elements for gene expression of the DIII nucleic acid. The regulatory elements can be a promoter, an enhancer an initiation codon, a stop codon, or a polyadenylation signal. Enhancers are often required for gene expression of the sequence that encodes the target protein or the immunomodulating protein. These elements can be operably linked to the sequence that encodes the desired proteins and the regulatory elements can be functional in the individual to whom they are administered.

The genetic construct, or vector, can also comprise a promoter that is operably linked to the DIII coding sequence. The promoter operably linked to the DIII coding sequence can be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter can also be a promoter from a human gene such as human actin, human myosin, human hemoglobin, human muscle creatine, or human metalothionein. The promoter can also be a tissue specific promoter, such as a muscle or skin specific promoter, natural or synthetic. Examples of such promoters are described in US patent application publication no. US20040175727, the contents of which are incorporated herein in its entirety.

The vector can also comprise a polyadenylation signal, which can be downstream of the DIII coding sequence. The polyadenylation signal can be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal can be a polyadenylation signal from a pCEP4 vector (Invitrogen, San Diego, Calif.).

The vector can also comprise an enhancer upstream of the DIII coding. The enhancer can be necessary for DNA expression. The enhancer can be human actin, human myosin, human hemoglobin, human muscle creatine or a viral enhancer such as one from CMV, HA, RSV or EBV. Polynucleotide function enhances are described in U.S. Pat. Nos. 5,593,972, 5,962,428, and WO94/016737, the contents of each are fully incorporated by reference.

Genetic constructs can be provided with mammalian origin of replication in order to maintain the construct extrachromosomally and produce multiple copies of the construct in the cell. Plasmids pVAX1, pCEP4 and pREP4 from Invitrogen (San Diego, Calif.) contain the Epstein Barr virus origin of replication and nuclear antigen EBNA-1 coding region which produces high copy episomal replication without integration. The backbone of the vector can be pAV0242. The vector can be a replication defective adenovirus type 5 (Ad5) vector.

The vector can also comprise a regulatory sequence, which can be well suited for gene expression in a mammalian or human cell into which the vector is administered. The DIII coding sequence can comprise an optimized codon, which can allow more efficient transcription of the coding sequence in the host cell.

The vector can be pSE420 (Invitrogen, San Diego, Calif.), which can be used for protein production in *Escherichia coli* (*E. coli*). The vector can also be pYES2 (Invitrogen, San Diego, Calif.), which can be used for protein production in *Saccharomyces cerevisiae* strains of yeast. The vector can also be of the MAXBAC™ complete baculovirus expression system (Invitrogen, San Diego, Calif.), which can be used for protein production in insect cells. The vector can also be pcDNA I or pcDNA3 (Invitrogen, San Diego, Calif.), which may be used for protein production in mammalian cells such as Chinese hamster ovary (CHO) cells. The vector can be expression vectors or systems to produce protein by routine techniques and readily available starting materials including Sambrook et al., Molecular Cloning an Laboratory Manual, Second Ed., Cold Spring Harbor (1989), which is incorporated fully by reference.

In order to maximize protein production, regulatory sequences may be selected which are well suited for gene expression in the cells the construct is administered into. Moreover, codons that encode said protein may be selected which are most efficiently transcribed in the host cell, i.e., codon optimized. One having ordinary skill in the art can produce DNA constructs that are functional in the cells.

In some embodiments, nucleic acid constructs may be provided in which the coding sequences for the proteins described herein are linked to IgE signal peptide. In some embodiments, proteins described herein are linked to IgE signal peptide.

The vector can be pVAX1-WNV DIII, pVAX1-JEV DIII, or pVAX1-JW DIII, all of which can be used for expressing the respective DIII antigen. The vector pVAX1-WNV DIII comprises the nucleotide sequence of SEQ ID NO: 5 or 13; the vector pVAX1-JEV DIII comprises the nucleotide sequence of SEQ ID NO: 4 or 12; and the vector pVAX1-JW DIII comprises the nucleotide sequence of SEQ ID NO: 6 or 14.

Method of Immunizing

In an aspect of the invention, there are methods of eliciting an immune response against a plurality of flavivirus virus serotypes in a host, comprising: (a) delivering the vaccines provided herein to the tissue of the host; and (b) electroporating cells of the tissue using an electroporation device that delivers a pulse of energy effective to permit entry of the genetic construct of the vaccine into the cells.

The vaccine can be administered to a mammal to elicit an immune response in a mammal. The mammal can be human, non-human primate, cow, pig, cattle, sheep, goat, antelope, bison, water buffalo, bison, bovids, deer, hedgehogs, elephants, llama, alpaca, mice, rats, or chicken, and preferably human, cow, pig, or chicken.

The DNA vaccines can be delivered using any of several well known technologies including DNA injection (also referred to as DNA vaccination) with and without in vivo electroporation, liposome mediated, nanoparticle facilitated, recombinant vectors such as recombinant adenovirus, recombinant adenovirus associated virus and recombinant vaccinia. Preferably, the nucleic acid molecules such as the DNA plasmids described herein are delivered via DNA injection and along with in vivo electroporation.

Routes of administration include, but are not limited to, intramuscular, intransally, intraperitoneal, intradermal, subcutaneous, intravenous, intraarterially, intraoccularly and oral as well as topically, transdermally, by inhalation or suppository or to mucosal tissue such as by lavage to vaginal, rectal, urethral, buccal and sublingual tissue. Preferred routes of administration include intramuscular, intraperitoneal, intradermal and subcutaneous injection. Genetic constructs may be administered by means including, but not limited to, traditional syringes, needleless injection devices, "microprojectile bombardment gone guns", or other physical methods such as electroporation ("EP"), "hydrodynamic method", or ultrasound.

Examples of electroporation devices and electroporation methods preferred for facilitating delivery of the DNA vaccines of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Also preferred, are electroporation devices and electroporation methods for facilitating delivery of the DNA vaccines provided in co-pending and co-owned U.S. patent application Ser. No. 11/874,072, filed Oct. 17, 2007, which claims the benefit under 35 USC 119(e) to U.S. Provisional Application Ser. Nos. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 are adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

The following is an example of methods of the present invention, and is discussed in more detail in the patent references discussed above: electroporation devices can be configured to deliver to a desired tissue of a mammal a pulse of energy producing a constant current similar to a preset current input by a user. The electroporation device comprises an electroporation component and an electrode assembly or handle assembly. The electroporation component can include and incorporate one or more of the various elements of the electroporation devices, including: controller, current waveform generator, impedance tester, waveform logger, input element, status reporting element, communication port, memory component, power source, and power switch. The electroporation component can function as one element of the electroporation devices, and the other elements are separate elements (or components) in communication with the electroporation component. In some embodiments, the electroporation component can function as more than one element of the electroporation devices, which can be in communication with still other elements of the electroporation devices separate from the electroporation component. The present invention is not limited by the elements of the electroporation devices existing as parts of one electromechanical or mechanical device, as the elements can function as one device or as separate elements in communication with one another. The electroporation component is capable of delivering the pulse of energy that produces the constant current in the desired tissue, and includes a feedback mechanism. The electrode assembly includes an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism can receive the measured impedance and can adjust the pulse of energy delivered by the electroporation component to maintain the constant current.

In some embodiments, the plurality of electrodes can deliver the pulse of energy in a decentralized pattern. In some embodiments, the plurality of electrodes can deliver the pulse of energy in the decentralized pattern through the control of the electrodes under a programmed sequence, and the programmed sequence is input by a user to the electroporation component. In some embodiments, the programmed sequence comprises a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

In some embodiments, the feedback mechanism is performed by either hardware or software. Preferably, the feedback mechanism is performed by an analog closed-loop circuit. Preferably, this feedback occurs every 50 μs, 20 μs, 10 μs or 1 μs, but is preferably a real-time feedback or instantaneous (i.e., substantially instantaneous as determined by available techniques for determining response time). In some embodiments, the neutral electrode measures the impedance in the desired tissue and communicates the impedance to the feedback mechanism, and the feedback mechanism responds to the impedance and adjusts the pulse of energy to maintain the constant current at a value similar to the preset current. In some embodiments, the feedback mechanism maintains the constant current continuously and instantaneously during the delivery of the pulse of energy.

EXAMPLES

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The DNA plasmids for use with the EP devices of the present invention can be formulated or manufactured using a combination of known devices and techniques, but preferably they are manufactured using an optimized plasmid manufacturing technique that is described in a commonly owned, U.S. provisional application U.S. Ser. No. 60/939,792, which was filed on May 23, 2007. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a commonly owned patent, U.S. Pat. No. 7,238,522, which issued on Jul. 3, 2007. Both U.S. Ser. No. 60/939,792 and U.S. Pat. No. 7,238,522 are hereby incorporated in their entirety.

Cell Lines

HeLa and RD cells were obtained from the American Type Culture Collection (Manassas, Va.). The cells were maintained in DMEM medium supplemented with 10% heat inactivated fetal bovine serum, penicillin G (100 U/ml), streptomycin (100 ug/ml) at 37° C. in 5 $CO_2$.

Indirect Immunofluorescent Assay

HeLa cells were used to perform an indirect immunofluorescent assay. The cells were seeded in a two-chamber slide and grown for overnight prior to their use in transfection. They were transfected with vaccine constructs or pVAX (1 mg/well) using FuGENE 6 Transfection Reagent (Roche). Thirty six hours post transfection, the cells were fixed with methanol for twenty minutes at room temperature and washed gently with PBS. They were incubated with anti-mouse the sera from vaccinated mice for 90 min and washed again. Subsequently, the samples were incubated with FITC-conjugated secondary antibody (Sigma-Aldrich) for 45 min. 40,6-Diamido-2-phenylindole hydrochloride (Sigma-Aldrich) was added to the solution of secondary antibody to counterstain nuclear contents in order to show the total number of cells available in the given field. The images were acquired using Phase 3 Pro program for fluorescent microscopy (Media Cybernetics, Silver Spring, Md.).

Statistical Analysis

All of the values are expressed as the mean±standard error of the mean (SEM) calculated from triplicate samples from each experimental group. Where appropriate, the statistical difference was assessed by using a two-tailed, paired Student's t Test and yielded a specific p value for each experimental group. Routinely the data shown were representative of at least three independent experiments done in duplicate or triplicate.

Example 1

Consensus DNA Vaccine Constructs and Synthesis

To generate JEV and WNV E DIII consensus sequences, approximately 15 different sequences were collected from different geographical regions from GeneBank (NCBI) to avoid sampling bias and aligned using MegAlign (DNASTAR, Madison, Wis.). IgE-leader sequence was added to the amino terminus of resulting consensus sequences and two stop codons were added at the end of the open reading frames. KpnI and PstI sites were tagged to 5' and 3' ends, respectively. The complete sequence was subjected to codon optimization and RNA optimization using GeneOptimizer (GENEART, Regensburg, Germany). The codon optimized synthetic sequences were then cloned into pVAX1 expression vector (Invitrogen) as described herein.

Cloning of Human IL-15ECRO into pVAX1 Vector and IL-15 Expression Analysis

Native IL-15 contains two alternative leader peptides that are not only involved in the regulation of IL-15 translation, but also direct its intracellular trafficking. The classical long (48 aa) signal peptide is associated with all secreted forms of IL-15, while IL-15 that contains the short 21 aa signal peptide is not secreted but rather stored intracellularly (1-4). Design for the plasmid form of optimized human IL-15 (pIL15 ECRO) requires replacing the LSP with an "optimized" IgE leader designed by our laboratory for increased protein expression (5, 6). Moreover, the codon usage was adapted to the codon bias of *Homo sapiens* genes resulting in a high CAI value (non optimized: 0.66; optimized: 0.98). Since human and mouse genes share 73% homology, we utilized pIL15 ECRO in vivo using the mouse model. For design and synthesis, codons were selected so that regions of very high (>80%) or very low (<30%) GC content was avoided where possible. In this regard, it has been determined that the wild type IL15 gene uses rare codons with a high frequency and the GC content was quite low (35%) which facilitates quick mRNA turnover. Therefore, GC-content was increased (57%) to prolong mRNA half-life. During the optimization process, the following cis-acting sequence motifs were avoided: internal TATA boxes, chi-sites and ribosomal entry sites, AT-rich or GC-rich sequence stretches, ARE, INS, CRS sequence elements, repeat sequences and RNA secondary structures, (cryptic) splice donor and acceptor sites and branch points. Following analysis, 3 negatively cis-acting motifs were identified and removed. The final design of the gene contained 100% congruence with mature form of human IL15 with IgE leader replacing the wild type LSP form. The synthetic highly optimized human IL15 gene was assembled from synthetic oligonucleotides by Geneart, Inc. (Germany). A Kozak sequence was introduced to increase translational initiation and two stop codons were added to ensure efficient termination. The fragment was cloned into pVAX1 μsing EcoRI and XhoI restriction sites. The final construct was verified by sequencing and found to be 100% congruence. One day before transfection, 7.0×105 HeLa or RD cells grown in D10 medium (DMEM, 20% FBS, 1% antibiotic) were seeded onto 60 mm culture dishes (Falcon).

The cells were then transfected with 5 ug of the IL-15 constructs with DOTAP liposome transfection kit (Roche Biochemicals, CA) according to the manufacturer's protocol. Supernatants were collected at 24, 48, and 72 hours post transfection and analyzed for protein levels via ELISA (R & D) as per the manufacturer's protocols.

Validation of Consensus Antigens

Prior to their application in vaccination studies following confirmation of sequence of inserts by sequencing, DIII vaccine constructs were validated for their ability to express their gene products with appropriate molecular mass. By using an in vitro translation/transcription system (Promega, Madison, Wis.), 35S-labeled radioactive protein products were generated from these constructs, immunoprecipitated, and resolved by SDS-PAGE. These plasmids generated gene products of about 16.5 kDa in mass corresponding to the predicted length of the open reading frame (FIG. 1D). In order to confirm the presence of appropriate mRNA transcripts by RT-PCR during their expression in cells, RD cells were transfected with either empty vector or pVAX1-borne DIII domain constructs. The presence of cDNA of about 420 bps from transfected cells expressing individual DIII-constructs was observed only from the cells transfected with the DIII constructs. Lack of corresponding signals from mock-transfected cells confirms the specificity of this assay (FIG. 1E). These results together validated JEV, WNV and JE/WNV DIII constructs and hence they were further subjected to immunization studies.

Expression Analysis of IL-15 ECRO Construct

Figure 2B:
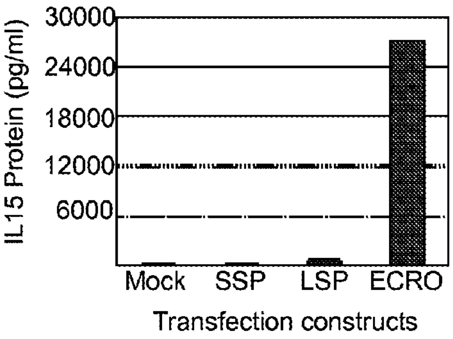
Figure 2C:
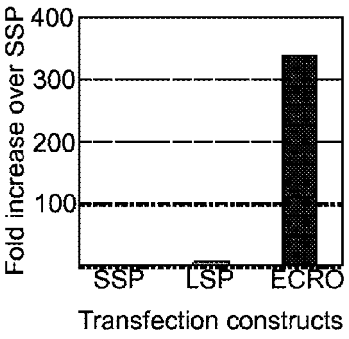

In order to confirm the localization pattern of IL15, HeLa cells were transfected with each of these IL15 constructs and subjected to immunofluorescent analysis using monoclonal anti-IL15 antibody. As anticipated, IL15 SSP has been retained within the nuclear region and both IL15 LSP and IL15 ECRO displayed cytoplasmic localization patterns (FIG. 2A). Next, a transfection assay in RD cells was carried out to compare the efficiency of IL15-constructs in their ability to express and secrete functional IL15. The data showed that a substantial increase in protein production and secretion (87-fold higher than the native IL-15, and 5.7-fold higher than the IL-15-LSP construct) were observed from the human-optimized construct, IL15 ECRO, as measured by specific ELISA analysis [33](FIG. 2B, C). These data clearly demonstrate that the pIL15 ECRO construct is highly efficient in expressing and secreting IL15 than all of the IL15 expressing plasmids that we have reported earlier.

Example 2

In Vitro Expression of Vaccine Constructs

The ability of constructs to generate their gene products with predicted molecular mass was confirmed prior to their use in vaccination studies. By utilizing T7-promoter in the pVAX1 backbone, the TNT T7 in vitro transcription/translation kit (Promega, Madison, Wis.) was used to generate 35S-methionine labeled protein samples as per the supplier's protocols. The radiolabeled protein samples were immunoprecipitated anti-WNV E or anti JEV E antibody and the immunoprecipitated complexes were electrophoresed on a 15% SDS-PAGE gel (BioRad). The gel was fixed using phosphoenhancer solution (Amersham) and dried using a vacuum drier (Biorad). Autoradiography was performed to detect incorporated an S35-labelled gene product.

FIG. 1A reveals schematically the organization of flaviviral polypeptide and the conformational features of E protein. In an effort to develop an immunogen with the ability to induce highly cross-reactive cellular responses, amino acid sequences JEV and WNV E DIII domain were downloaded from public databases. The sequences were chosen from diverse geographical locations and were non-recombinant. MegAlign (DNASTAR, Madison, Wis.) program was used to align the amino acid sequences and the most common amino acid at each position was chosen. We generated three constructs, a consensus WNV DIII construct, consensus JEV DIII construct and a chimeric JEV construct in which several residues from WNV DIII that were shown to be determinants of inducing neutralizing antibodies were incorporated at their corresponding positions of JEV DIII, without altering the length of DIII fragment; this antigen is referred as JE/WNV DIII domain (FIG. 1B). The rationale for this chimeric clone was to have a single vaccine construct that could provide enhanced immunity to both WNV and JEV together, instead of two individual vaccine constructs. After generation of the consensus sequence, an IgE leader sequence was fused to the amino terminus of the DIII domain coding sequence. Based on the amino acid sequence, human optimized synthetic gene sequences were constructed was created for all three vaccine constructs, and cloned into the pVAX vector (FIG. 1C).

Example 3

Bacterial Expression E DIII Proteins

The DIII coding regions were released from their pVAX backbone by digestion with KpnI/PstI. The released fragments were gel-purified, then ligated into pQE-30 digested with KpnI/PstI. The ligation products were transformed into JM109 cells, which were plated on LB agar plates containing 50 ug/ml ampicillin. Colonies formed overnight at 37° C. Glycerol stocks were prepared from individual colonies. For protein expression, a 3 ul aliquot of glycerol stock was added to a 16×150 mm tube containing 6 milliliters of LB broth containing 50 ug/ml ampicillin. The resulting bacterial pellet is processed and the lysates are passed through Ni-columns as per the standard protocols for accomplishing purification of the proteins samples. The resulting purified protein samples will be used as coating antigens for ELISA as well as B-cell proliferation ELISpot assays.

Production of JEV, WNV and JE/WNV DIII Proteins

Figure 3:
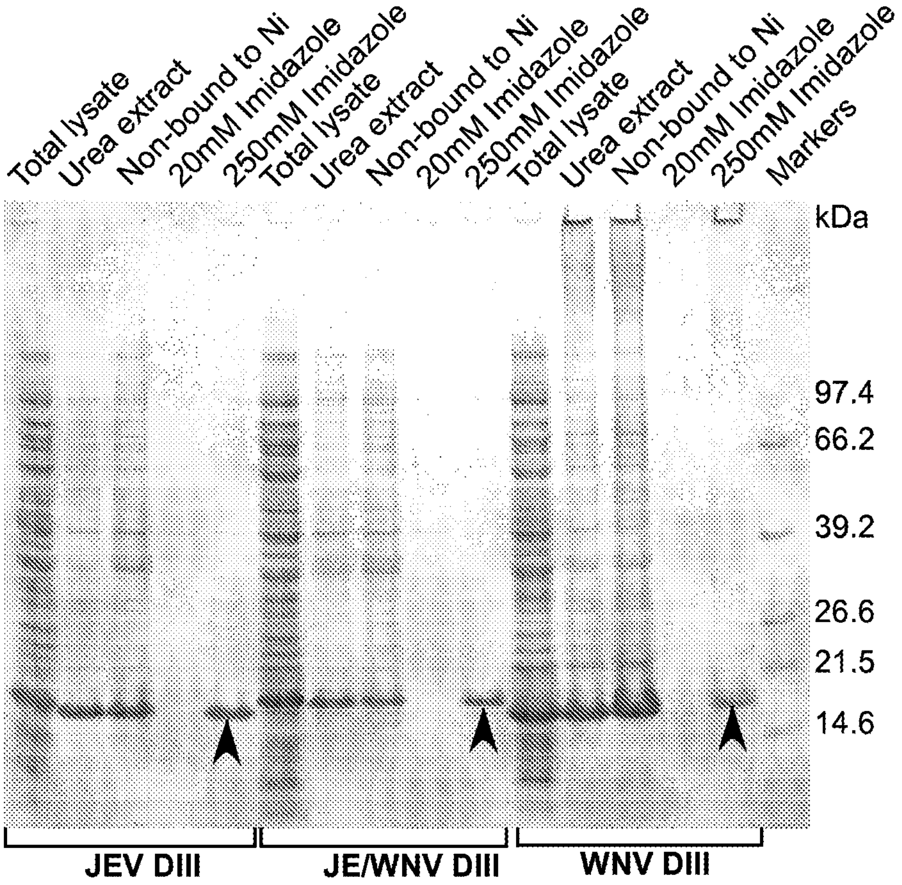
FIG. 3: Bacterial production and purification of DIII protein fragments. DIII-encoding regions were cloned into pQE30-expression vector and protein samples were purified from bacterial lysates as described in Materials and Methods. Coomassie staining of PAGE indicating the samples collected from different stages of purification process in a bacterial expression system. After binding to the Ni-column, elusion buffer with 20 mM-Imidazole failed to release DIII fragments and imidazole at 250 mM was effective in selectively eluting histidine tagged-DIII fragments. The prominent bands of purified DIII fragments with appropriate molecular mass (16.5 kDa) are marked.

The DIII-encoding fragments were subcloned into a bacterial expression vector, and the protein fragments were purified using Ni-chelated columns as described herein. FIG. 3 describes the purity level of DIII fragments from different purification steps. The lanes containing crude lysates from DIII-expressing bacterial cells indicated that even without IPTG induction, the level of the expression of DIII fragment was very prominent. In comparison to the ladder of samples present from total crude sample lanes, a distinct single band that corresponded to the mass of 16 kDa was observed from the eluted fractions containing 250 mM imidazole indicating a high level of purity of the expressed DIII fragments. Imidazole at 20 mM was not sufficient to release His-tagged DIII samples from Ni-chelated matrix. Hence the choice of imidazole in the elution buffer was very specific to the elution of the His-tagged protein. The purified fractions were dialyzed and stored in aliquots upon determination of their concentration for their subsequent applications as coating antigens in this study.

Example 4

Mice and Immunization

Female 6-8-week-old C57BL/6 mice were purchased from the Jackson laboratory. The quadriceps muscles of 6-8 week-old female BALB/c mice (Charles River, Wilmington, Mass.) were injected three times and electroporated, each with 10 μg of DNA at biweekly intervals. For DNA immunizations, the mice were separated into groups of five mice each and immunized by electroporation with pIL15 ECRO and pVAX (control group) or pJEV DIII, pJE/WNV DIII, pWNV DIII, and pJEV DIII+pWNV DIII, respectively.

Briefly, square-wave pulses were used and delivered with the constant-current CELLECTRA® electroporator (VGX Pharmaceuticals Inc., Blue Bell, Pa.). A three electrode array (3-EA) was used and it consists of three 26-gauge solid stainless steel electrodes in an isosceles triangle formation, with the two long sides 0.5 mm in length and short side 0.3 mm in length, held together with a nonconductive plastic. The sequence of events for plasmid administration/EP was as follows: place a disposable electrode array in the receptacle of the handle, press initiation button on handle and enter animal experimental group number, inject DNA plasmid using insulin syringe, immediately place the array into area surrounding the injection site, press initiation button on handle, and after 4 s countdown, pulses will be delivered. The EP conditions were 0.2 Amps, 2 pulses, 52 ms/pulse, 1 s between pulses. All electrodes were completely inserted into the muscle during all treatments. All DNA was made using endotoxin-free Qiagen columns. Mice were housed and treated at the University of Pennsylvania, and cared for under the guidelines of the NIH and the University of Pennsylvania Institutional Animal Care and Use Committee (IACUC).

Titration of Anti-DIII Antibodies from DNA Vaccinated Sera

Figure 4A:
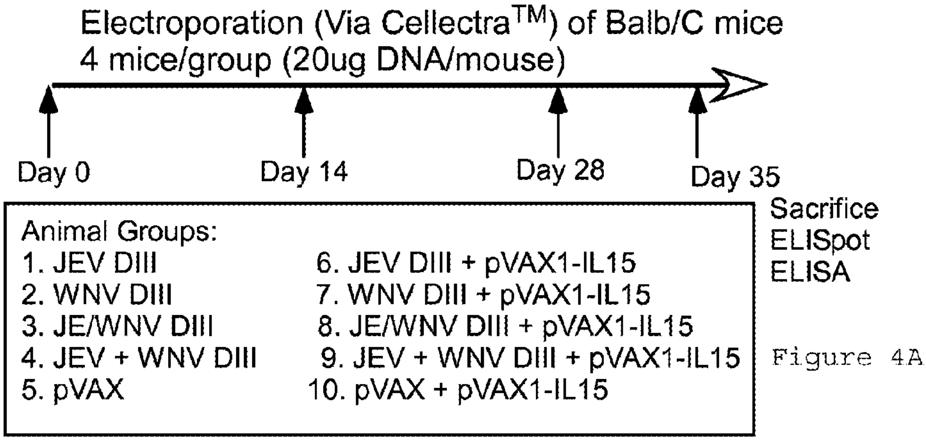
FIGS. 4A-B.

In vivo electroporation (IVE) for the delivery of DNA vaccines was combined with the consensus antigens to induce a potent immune response against synthetic DNA antigens. Balb/c mice were immunized and electroporated with each of the individual vaccine candidates in the presence or absence of pIL15 ECRO (FIG. 4A). Serum samples from DNA-vaccinated mice obtained one week after third booster were assayed for the presence of respective antibody against JEV and WNV by ELISA. All of the vaccinated mice had produced antibodies against DIII domains. Sera from the entire DNA vaccinated mice were evaluated individually against all three antigens: JEV DIII, WNV DIII and JE/WNV DIII.

Figure 4B:
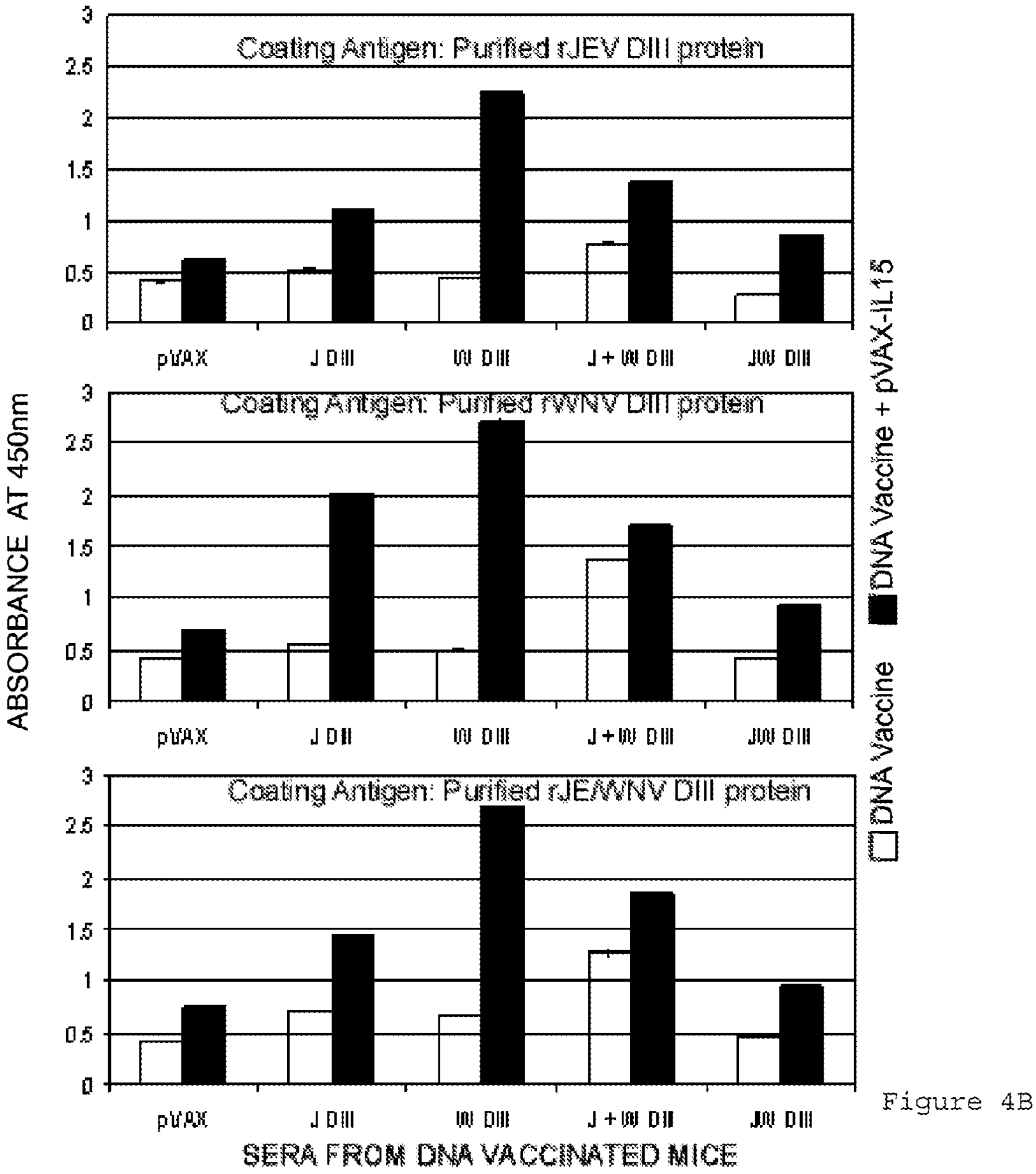

As shown in FIG. 4B, ELISA data has yielded interesting results. First, this assay indicated that the coimmunization of DIII constructs with IL15-plasmid has significantly enhanced antibody production against both JEV and WNV DIII antigens. Comparatively, the addition of IL15 has induced the highest level of response against WNV DIII. Second, in the animal group that was not coimmunized with IL15, the combination of JEV and WNV DIII expression plasmids induced higher level of antibody production than the response elicited by these two vaccine constructs individually. Third, with respect to the chimeric JEV/WNV construct, the antibody production was found to be significantly lower. IL15 did not appear to exert its positive effect on this chimeric construct. Thus, this chimeric JEV/WNV antigen failed to serve as a potential antigen for inducing a strong antibody immune response, not only against JEV DIII and WNV DIII, but against the chimeric protein itself. Overall, the antibody titer from the animals that received the cocktail of WNV DIII and IL15 constructs was very high, and most importantly serum from group could bind to all three antigens consistently demonstrating the broad reactivity induced by this construct.

Example 5

DIII Antibody ELISA Assay

The DIII protein suspensions were thawed, and the tubes were vortexed to suspend to the fine protein particulates. Small aliquots of the resuspended protein samples were dissolved in Buffer TU (62 mM Tris-HCl/8M urea, pH 8.0) to produce a 10 ug/ml solution. Aliquots of 100 ul (1 ug) of diluted protein samples were applied to the wells of a Pierce HisGrab Copper Coated High Binding Capacity Plate and incubated for overnight at 4° C. The next day, plates were washed with PBST (PBS, 0.05% Tween 20), blocked for 1 h with 3% BSA in PBST, and incubated with serial dilutions of serum from immunized and naive mice for 1 h at 37° C. Bound IgG was detected using goat anti-mouse IgG-HRP (Research Diagnostics, NJ) at a dilution of 1:10,000. Bound enzyme was detected by the addition of the chromogen substrate solution tetramethylbenzidine (TMB; R&D Systems), and read at 450 nm on a Biotek EL312e Bio-Kinetics reader. All serum samples were tested in duplicate.

Specificity of Anti-DIII Sera to DIII-Expressing Transfected Cells

Figure 5A:
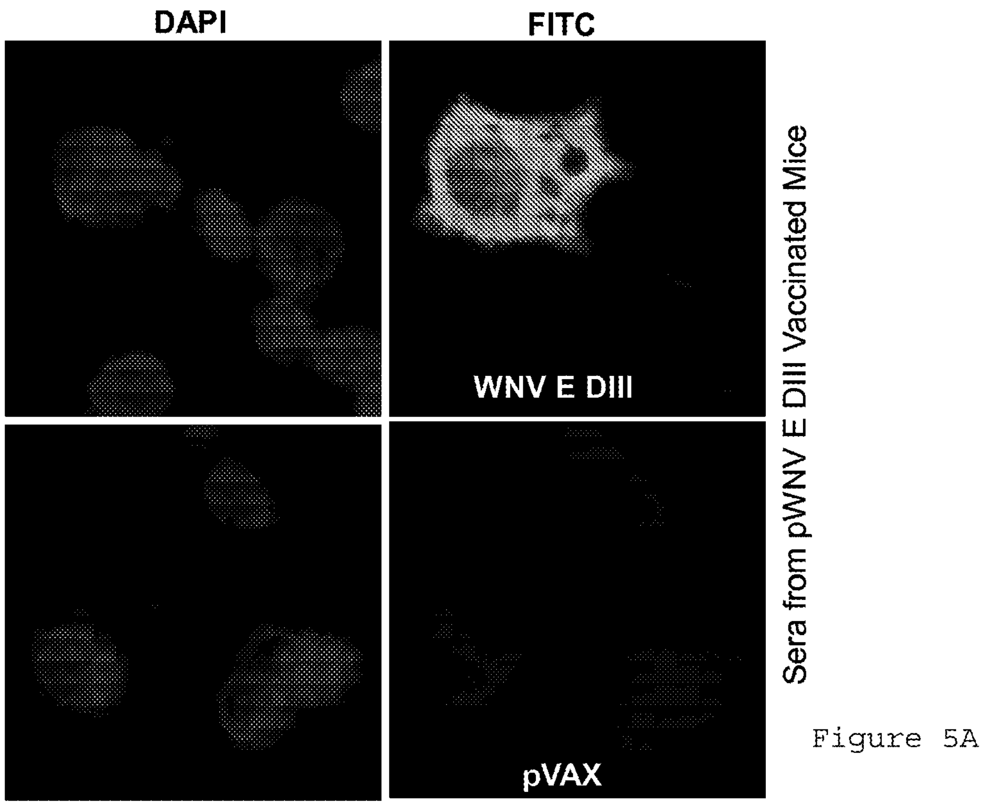
FIGS. 5A-B: Staining of DIII-transfected cells with sera from DNA-vaccinated mice. HeLa cells were transfected with pVAX or pWNV DIII (slides in FIG. 5A) or pJEV DIII (slides in FIG. 5B) expressing vaccine constructs. Two days post transfection, they were fixed and incubated with serum from BALB/c mice immunized with these DNA vaccine constructs. Subsequently they were incubated with FITC-conjugated anti-mouse secondary antibody and DAPI which counter stains nuclear contents of the cells. Lack of appropriate staining by pVAX-serum sample is presented below each set.
Figure 5B:
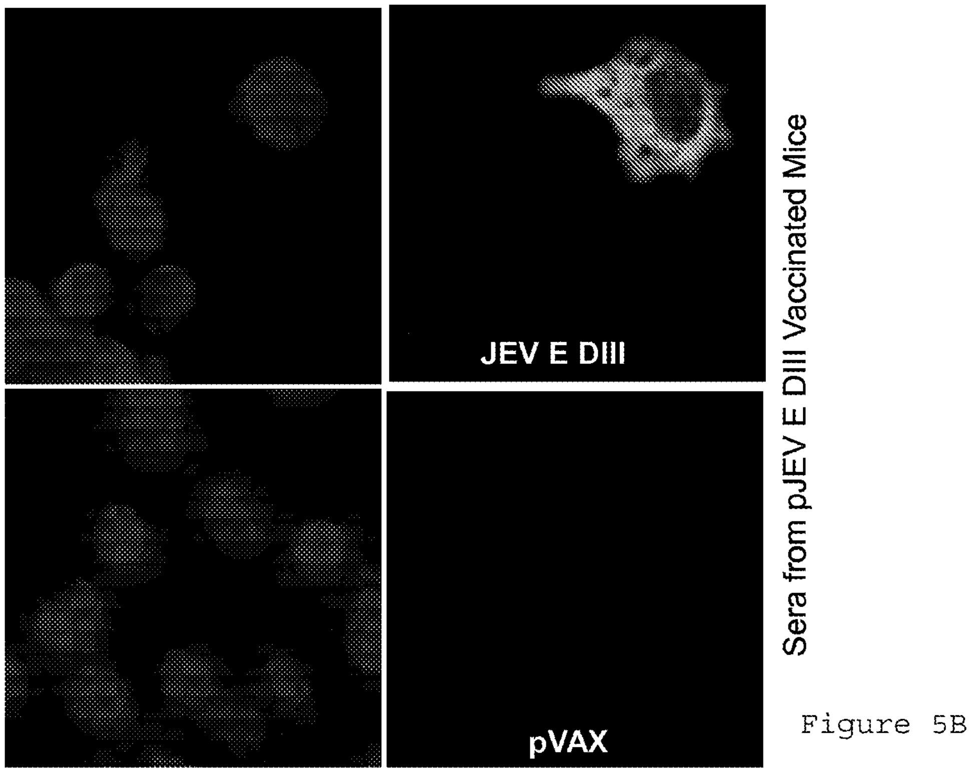

Serum from DNA vaccinated mice were also examined to verify whether it can bind to the DIII antigens expressed in cells that were transfected with these vaccine constructs. For this purpose, HeLa cells were transiently transfected with all three DIII-encoding pVAX expression constructs and thirty six hours post transfection, the cells were fixed for immunofluorescence analysis (see above-described methods). The cells were first incubated with appropriate serum samples followed by FITC-conjugated antimouse secondary antibody. The nuclear content of the cells were counterstained with DAPI in order to know the total number of cells available in a given field. Anti-DIII sera from DNA vaccinated mice stained only the transfected cells that expressed WNV (FIG. 5A) and JEV DIII (FIG. 5B). The staining pattern resembled that of prototypic expression of flaviviral E[35]. Mostly importantly, the DIII expressing cells revealed a predominantly cytoplasmic localization pattern. Anti-DIII-serum did not show any significant staining with either untransfected or pVAX1-transfected HeLa cells.

Example 6

Splenocyte Purification

Mice were sacrificed one week after the third immunization and the spleens from each mouse were harvested and pooled in a 15 ml conical containing RPMI 1640 (one tube for each experimental group). In a sterile tissue culture hood, the pooled spleens from each experimental group were placed in a petri dish and crushed in a sterile bag using Stomacher blender (Brinkmann Instruments, Inc). The splenocytes were washed and pelleted (1200 rpm); the pellet was treated with ACK lysing buffer (Biosource) for 5-10 minutes, and then washed, pelleted (1200 rpm) and put through a 70 μm cell strainer to remove any remaining spleen organ stroma. The splenocytes were washed in RPMI 1640 twice, resuspended in R10 medium (RPMI 1640 plus 10% FBS), and counted (cell viability is determined using trypan blue stain) using a hemocytometer.

Example 7

Memory B Cell ELISpot Assay

The ELISpot 96-well plates (Millipore) were coated with 100 μl (2 μg/ml) of purified proteins and incubated for overnight at 4° C. Separate plates were used each coating antigen. The following day, plates were washed and blocked for 2 h with 1% BSA. Two hundred and fifty thousand splenocytes from the immunized mice were added to each well and stimulated for 5-6 hours at 37° C. in 5% CO2 in the presence of RPMI 1640 (negative control). Following incubation, the cells were washed and incubated for overnight at 4° C. with biotinylated anti-mouse antibody (R&D Systems). The plates were washed, and streptavidin-alkaline phosphatase (R&D Systems) was added to each well and incubated for 2 h at room temperature. The plates were again washed, and 5-bromo-4-chloro-3'-indolylphosphate p-toluidine salt and nitro blue tetrazolium chloride (chromogen color reagent; R&D Systems) were added to each well. The plate was then rinsed with distilled water and dried at room temperature. Spots were counted by an automated ELISPOT reader (Cellular Technology Limited). Results are expressed as a number of antigen-specific antibody secreting cells (ASCs).

IL15 Enhanced Memory B-Cell Activation Against JEV and WNV Antigens.

Figure 6:
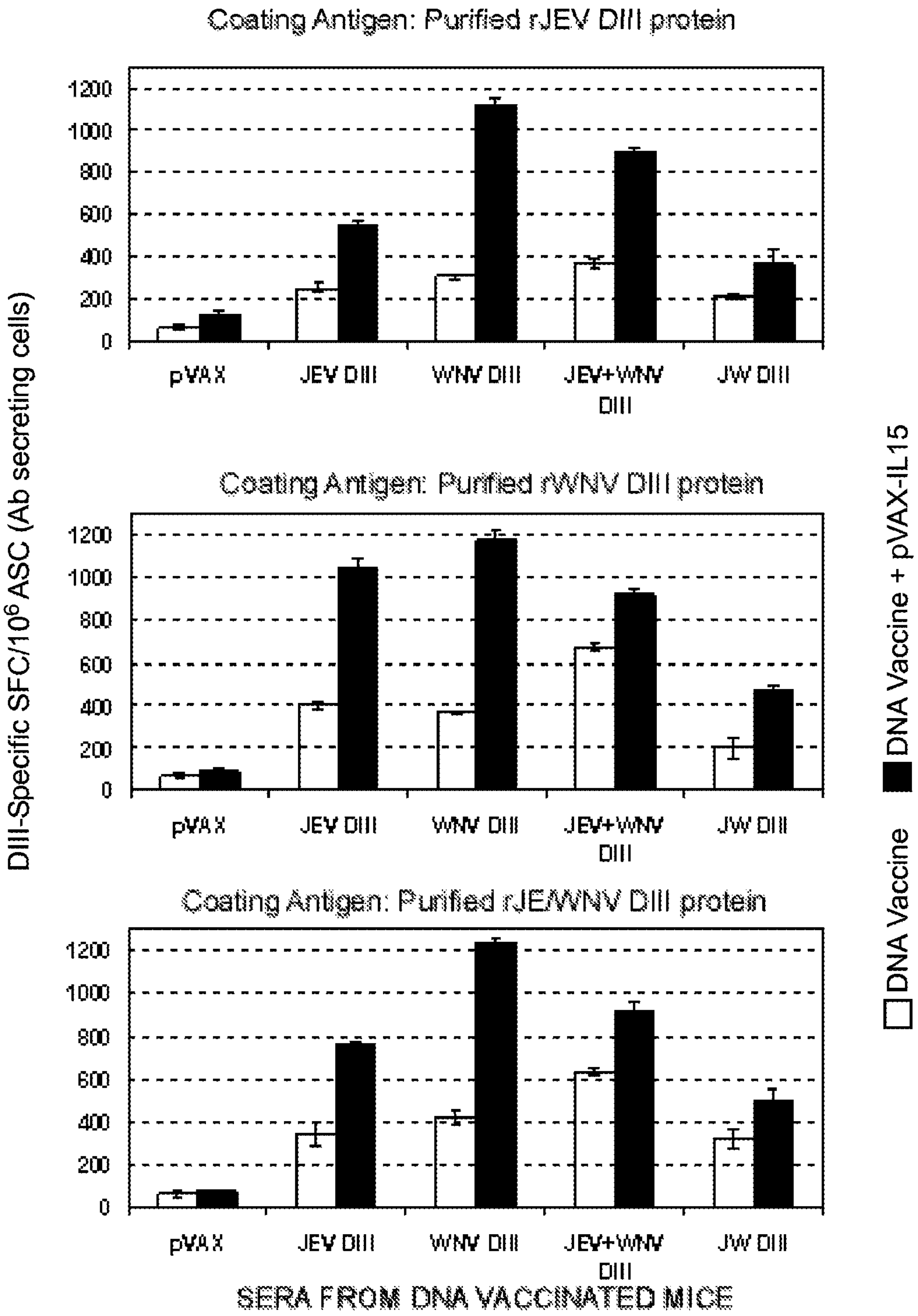
FIG. 6: E DIII ELISpot. BALB/c mice were immunized three times, each 2 weeks apart, with 20 μg pVAX vector or DIII-expression constructs and sacrificed 1 week later. Splenocytes were harvested and cultured overnight in the presence of R10 (negative control) or 2 μg/ml of one of three purified DIII protein samples. Spot forming units were quantified by an automated ELISPOT reader, and the raw values were normalized to SFU per million splenocytes. Values represent the mean (±}S.D.) of triplicate wells.
Figure 7:
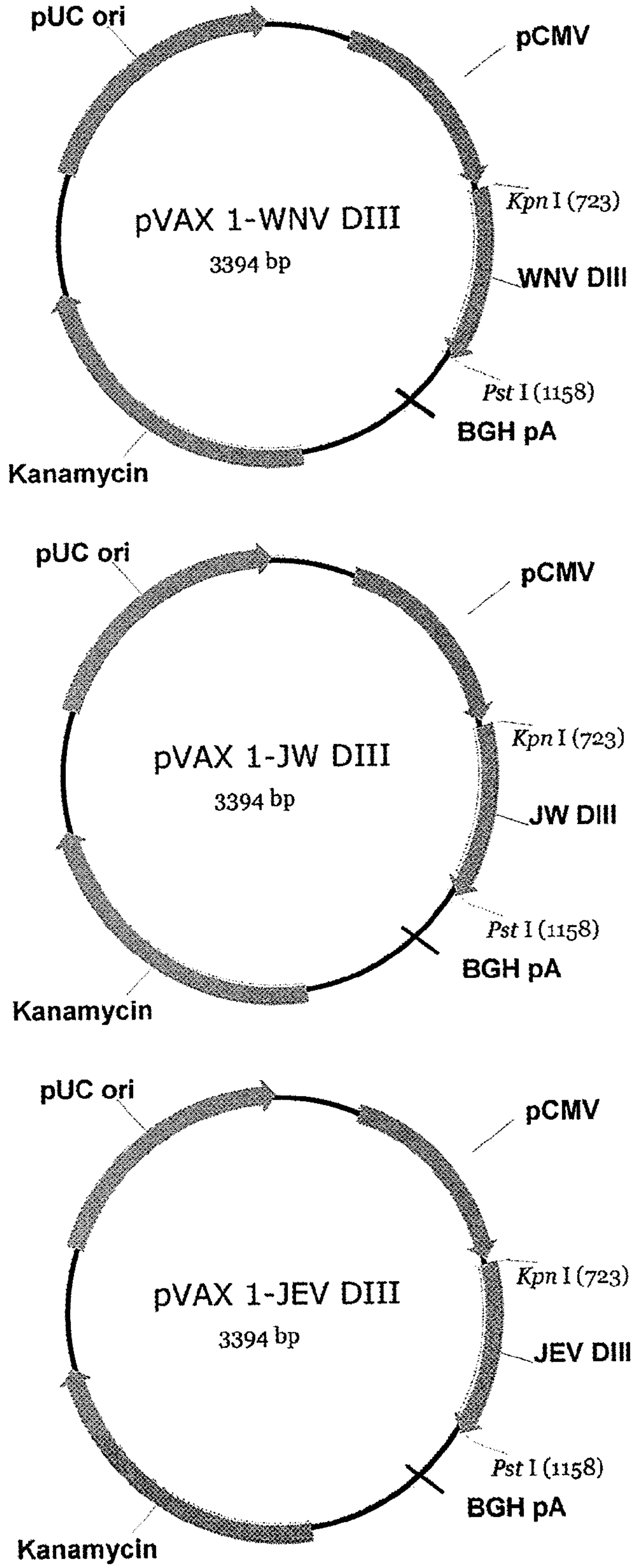
FIG. 7: Displays the plasmid maps for DNA constructs pVAX1-WNV DIII, pVAX1-JEV DIII, and the chimeric construct pVAX1-JW DIII.

The B cell ELISPOT technology allows the quantification of antigen-specific memory B cells by inducing the in vitro differentiation of B-memory cells into antibody secreting plasma cells following stimulation with appropriate antigen. To further evaluate the quality of the immune response induced by IL15 adjuvant, the B-memory response was evaluated in mice. Mouse spleens were prepared to measure the frequency of B cells capable of producing antibodies directed against DIII proteins, as described in "Methods". Interestingly ELISpot assay results concur with DIII-antibody ELISA data that were described above. Higher frequencies of mouse antibody secreting cells specific for DIII were observed in mice that were co-stimulated with IL15 than the groups that received DIII DNA vaccine alone (FIG. 6). This assay also suggested that IL15 has clearly boosted antibody secreting cell responses against pWNV DIII vaccine, as evidenced that this group exhibited the highest level of antibody secreting cells. Most importantly B cells from WNV DIII+IL15 group could bind to all three antigens, as observed with ELISA data from sera from this group of animals. Next to this group, JEV DIII+IL15 displayed enhanced level of B-cell response than the mice received JEV DIII alone. In line with the ELISA results from chimeric JE/WNV DIII vaccinated mice, B cells from this group of mice failed to bind not only to JEV or WNV DIII-vaccinated mice, but to the group that this received chimeric antigen itself. Taken together, the ELISpot results indicated the activation of high-affinity antigen specific B cells that corresponded to the titers of DIII-specific antibodies as determined by ELISA studies.

The results from our study agree with this possibility that DIII protein sample may not be a better vaccine candidate. One possible interpretation is that the percentage of solubilized proteins that folded correctly might be low and the purification procedures followed by different investigators also may affect immunogenicity of rDIII. Without IL15 support, we could not find satisfactory antibody response from the use of monomeric DIII expressing constructs. In this study, we showed enhanced level of B-cell proliferation as well as antibody production by using only 20 ug DNA per animal. Hence DNA vaccine in combination with IL15 plasmid could represent a better, cost effective alternate for immunization against JEV and WNV.

Collectively the results obtained in the present study indicate that DIII is a promising well defined vaccine candidate that in combination with a good adjuvant can use used for the induction of protective immunity against WNV and JEV. Four to five fold increase in the level of antibody producing cells due to the costimulation of IL15 provided direct evidence that IL15 can induce the production of neutralizing antibody through enhancing antibody producing memory B cells against WNV as well as JEV. In contrary to the rationale that we set forth for making chimeric DIII protein, the resulting chimeric protein did not serve as a better antigen as noted from failed antibody response and the least number of antibody-producing memory B cells. One possible reason could be that introduction of epitopes from WNV DIII into JEV DIII might have affected the conformation status that is needed for proper presentation for eliciting immune response. That is why this chimeric protein underperformed in inducing immune response in comparison with its precursor molecules such as native JEV and WNV DIIIs. IL-15 has not been used systemically in any human study to date. It should be noted that recently, IL-15 has been implicated as a mediator of synovial inflammation, rheumatoid arthritis, autoimmune thyroiditis, and autoimmune diabetes. McInnes et al. as well as other laboratories have reported high concentrations of IL-15 in the synovial fluid of rheumatoid arthritic joints and showed that IL-15 is expressed by cells of the synovial membrane lining. To date, there have been no human studies that directly correlate a causal relationship of IL-15 to the induction of autoimmune disease. We have determined that injection of pIL-15-Opt results in undetectable levels of anti-human IL-15 Ab in the sera of mice, and we are unable to detect human IL-15 in the sera of vaccinated mice (unpublished observations), suggesting that the levels of IL-15 produced after vaccination with pIL-15-Opt are very low, but locally sufficient to enhance DIII-specific immune response observed in this study.

This report demonstrates a method by which an optimized cytokine plasmid-delivered IL-15 could enhance memory B cells specific to flaviviral DIII which is known for its role in inducing neutralizing antibody response.

REFERENCES

[1] Solomon T. Exotic and emerging viral encephalitides. Curr Opin Neurol 2003; 16(3):411-8.

[2] Solomon T. Recent advances in Japanese encephalitis. J Neurovirol 2003; 9(2):274-83.

[3] Harrington T, Kuehnert M J, Kamel H, Lanciotti R S, Hand S, Currier M, et al. West Nile virus infection transmitted by blood transfusion. Transfusion 2003 August; 43(8):1018-22.

[4] Armstrong W S, Bashour C A, Smedira N G, Heupler F A, Hoeltge G A, Mawhorter S D, et al. A case of fatal West Nile virus meningoencephalitis associated with receipt of blood transfusions after open heart surgery. The Annals of thoracic surgery 2003 August; 76(2):605-7.

[5] Shepherd J C, Subramanian A, Montgomery R A, Samaniego M D, Gong G, Bergmann A, et al. West Nile virus encephalitis in a kidney transplant recipient. Am J Transplant 2004 May; 4(5):830-3.

[6] Pealer L N, Marfin A A, Petersen L R, Lanciotti R S, Page P L, Stramer S L, et al. Transmission of West Nile virus through blood transfusion in the United States in 2002. The New England journal of medicine 2003 Sep. 25; 349(13): 1236-45.
[7] Kumar R, Tripathi P, Singh S, Bannerji G. Clinical features in children hospitalized during the 2005 epidemic of Japanese encephalitis in Uttar Pradesh, India. Clin Infect Dis 2006 Jul. 15; 43(2):123-31.
[8] Murgod U A, Muthane U B, Ravi V, Radhesh S, Desai A. Persistent movement disorders following Japanese encephalitis. Neurology 2001 Dec. 26; 57(12):2313-5.
[9] Schioler K L, Samuel M, Wai K L. Vaccines for preventing Japanese encephalitis. Cochrane database of systematic reviews (Online) 2007 (3):CD004263.
[10] Appaiahgari M B, Saini M, Rauthan M, Jyoti, Vrati S. Immunization with recombinant adenovirus synthesizing the secretory form of Japanese encephalitis virus envelope protein protects adenovirus-exposed mice against lethal encephalitis. Microbes and infection/Institut Pasteur 2006 January; 8(1):92-104.
[11] Bharati K, Vrati S. Japanese encephalitis: development of new candidate vaccines. Expert review of anti-infective therapy 2006 April; 4(2):313-24.
[12] Hoke C H, Nisalak A, Sangawhipa N, Jatanasen S, Laorakapongse T, Innis B L, et al. Protection against Japanese encephalitis by inactivated vaccines. The New England journal of medicine 1988 Sep. 8; 319(10):608-14.
[13] Takahashi H, Pool V, Tsai T F, Chen R T. Adverse events after Japanese encephalitis vaccination: review of post-marketing surveillance data from Japan and the United States. The VAERS Working Group. Vaccine 2000 Jul. 1; 18(26):2963-9.
[14] Diagana M, Preux P M, Dumas M. Japanese encephalitis revisited. Journal of the neurological sciences 2007 Nov. 15; 262(1-2):165-70.
[15] Heinz F X, Mandl C W, Holzmann H, Kunz C, Harris B A, Rey F, et al. The flavivirus envelope protein E: isolation of a soluble form from tick-borne encephalitis virus and its crystallization. Journal of virology 1991 October; 65(10): 5579-83.
[16] Nybakken G E, Oliphant T, Johnson S, Burke S, Diamond M S, Fremont D H. Structural basis of West Nile virus neutralization by a therapeutic antibody. Nature 2005 Sep. 29; 437(7059):764-9.
[17] Oliphant T, Engle M, Nybakken G E, Doane C, Johnson S, Huang L, et al. Development of a humanized monoclonal antibody with therapeutic potential against West Nile virus. Nature medicine 2005 May; 11(5):522-30.
[18] Martina B E, Koraka P, van den Doel P, Rimmelzwaan G F, Haagmans B L, Osterhaus A D. DC-SIGN enhances infection of cells with glycosylated West Nile virusin vitro and virus replication in human dendritic cells induces production of IFN-alpha and TNF-alpha. Virus research 2008 Apr. 9.
[19] Martina B E, Koraka P, van den Doel P, van Amerongen G, Rimmelzwaan G F, Osterhaus A D. Immunization with West Nile virus envelope domain III protects mice against lethal infection with homologous and heterologous virus. Vaccine 2008 Jan. 10; 26(2):153-7.
[20] Chu J H, Chiang C C, Ng M L. Immunization of flavivirus West Nile recombinant envelope domain III protein induced specific immune response and protection against West Nile virus infection. J Immunol 2007 Mar. 1; 178(5): 2699-705.
[21] Mota J, Acosta M, Argotte R, Figueroa R, Mendez A, Ramos C. Induction of protective antibodies against dengue virus by tetravalent DNA immunization of mice with domain III of the envelope protein. Vaccine 2005; 23(26): 3469-76.
[22] Yan J, Yoon H, Kumar S, Ramanathan M P, Corbitt N, Kutzler M, et al. Enhanced cellular immune responses elicited by an engineered HIV-1 subtype B consensus-based envelope DNA vaccine. Mol Ther 2007 February; 15(2):411-21.
[23] Laddy D J, Yan J, Corbitt N, Kobasa D, Kobinger G P, Weiner D B. Immunogenicity of novel consensus-based DNA vaccines against avian influenza. Vaccine 2007 Apr. 20; 25(16):2984-9.
[24] Weiner D B, Kennedy R C. Genetic vaccines. Scientific American 1999; 281(1):50-7.
[25] Schoenly K A, Weiner D B. Human immunodeficiency virus type 1 vaccine development: recent advances in the cytotoxic T-lymphocyte platform "spotty business". Journal of virology 2008 April; 82(7):3166-80.
[26] Boyer J D, Robinson T M, Kutzler M A, Vansant G, Hokey D A, Kumar S, et al. Protection against simian/human immunodeficiency virus (SHIV) 89.6P in macaques after coimmunization with SHIV antigen and IL-15 plasmid. Proceedings of the National Academy of Sciences of the United States of America 2007 Nov. 20; 104(47):18648-53.
[27] Draghia-Akli R, Khan A S, Brown P A, Pope M A, Wu L, Hirao L, et al. Parameters for DNA vaccination using adaptive constant-current electroporation in mouse and pig models. Vaccine 2008 Apr. 15.
[28] Nishimura H, Fujimoto A, Tamura N, Yajima T, Wajjwalku W, Yoshikai Y. A novel autoregulatory mechanism for transcriptional activation of the IL-15 gene by a nonsecretable isoform of IL-15 generated by alternative splicing. Faseb J 2005 January; 19(1):19-28.
[29] Yajima T, Nishimura H, Sad S, Shen H, Kuwano H, Yoshikai Y. A novel role of IL-15 in early activation of memory CD8+ CTL after reinfection. J Immunol 2005 Mar. 15; 174(6):3590-7.
[30] Ugen K E, Kutzler M A, Marrero B, Westover J, Coppola D, Weiner D B, et al. Regression of subcutaneous B16 melanoma tumors after intratumoral delivery of an IL-15-expressing plasmid followed by in vivo electroporation. Cancer gene therapy 2006 October; 13(10):969-74.
[31] Kutzler M A, Robinson T M, Chattergoon M A, Choo D K, Choo A Y, Choe P Y, et al. Communization with an optimized IL-15 plasmid results in enhanced function and longevity of CD8 T cells that are partially independent of CD4 T cell help. J Immunol 2005 Jul. 1; 175(1):112-23.
[32] Schluns K S, Lefrancois L. Cytokine control of memory T-cell development and survival. Nature reviews 2003 April; 3(4):269-79.
[33] Oya A, Kurane I. Japanese encephalitis for a reference to international travelers. J Travel Med 2007 July-August; 14(4):259-68.
[34] Hemmerter S, Slapeta J, van den Hurk A F, Cooper R D, Whelan P I, Russell R C, et al. A curious coincidence: mosquito biodiversity and the limits of the Japanese encephalitis virus in Australasia. BMC evolutionary biology 2007; 7:100.
[35] Solomon T, Dung N M, Wills B, Kneen R, Gainsborough M, Diet T V, et al. Interferon alfa-2a in Japanese encephalitis: a randomised double-blind placebo-controlled trial. Lancet 2003 Mar. 8; 361(9360):821-6.
[36] Solomon T, Ni H, Beasley D W, Ekkelenkamp M, Cardosa M J, Barrett A D. Origin and evolution of Japanese encephalitis virus in southeast Asia. Journal of virology 2003 March; 77(5):3091-8.
[37] Tsarev S A, Sanders M L, Vaughn D W, Innis B L. Phylogenetic analysis suggests only one serotype of Japanese encephalitis virus. Vaccine 2000 May 26; 18 Suppl 2:36-43.

The invention claimed is:

1. An isolated nucleic acid that encodes a consensus DIII domain of protein E from the flavivirus family comprising:
   nucleotides 7 to 366 of SEQ ID NO:13 or a complement thereof.

2. The isolated nucleic acid sequence of claim 1, wherein the nucleic acid is nucleotides 7 to 366 of SEQ ID NO:13.

3. A genetic construct comprising the isolated nucleic acid sequence of claim 2.

4. The genetic construct of claim 3 further comprising a Kozak sequence SEQ ID NO:15.

5. The genetic construct of claim 3 further comprising a leader sequence that is selected from a portion of IgG or IgE.

6. The genetic construct of claim 5, wherein the leader sequence comprises the nucleic acid sequence of SEQ ID NO.8.

7. A DNA vaccine against a plurality of WNV and JEV serotypes, the vaccine comprising:
   (a) a genetic construct comprising a promoter operably linked to a coding sequence comprising the nucleic acid of claim 1; and
   (b) a pharmaceutically acceptable excipient,
   wherein the genetic construct is capable of expressing the consensus DIII domain of protein E antigen in a cell of the host in a quantity effective to elicit an immune response.

8. The vaccine of claim 7, wherein the genetic construct further comprises a polyadenylation sequence following the 3' end of the coding sequence.

9. The vaccine of claim 7, wherein the genetic construct is codon optimized.

10. The vaccine of claim 7, wherein the pharmaceutically acceptable excipient is an adjuvant.

11. The vaccine of claim 10, wherein the adjuvant is selected from the group consisting of IL-2, IL-15, IL-28, and RANTES.

12. A method of eliciting an immune response against a plurality of flavivirus virus serotypes in a host, comprising:
   (a) delivering the vaccine of claim 7 to the tissue of the host; and
   (b) electroporating cells of the tissue using an electroporation device that delivers a pulse of energy effective to permit entry of the genetic construct of the vaccine into the cells.

13. The method of claim 12, wherein step (a) comprises injecting the vaccine into intradermic, subcutaneous, or muscle tissue.

14. The method of claim 12, wherein the current is preset for delivering to the tissue a pulse of energy at a constant current that equals the preset current.

15. The method of claim 12, wherein the electroporating step further comprises:
   (a) measuring the impedance in the electroporated cells;
   (b) adjusting the energy level of the pulse of energy relative to the measured impedance to maintain a constant current in the electroporated cells;
   wherein the measuring and adjusting steps occur within a lifetime of the pulse of energy.

16. The method of claim 12, wherein the electroporation step comprise delivering the pulse of energy to a plurality of electrodes according to a pulse sequence pattern that delivers the pulse of energy in a decentralized pattern.

17. The genetic construct of claim 5, wherein the genetic construct comprises SEQ ID NO:5.

* * * * *